US011793472B2

(12) United States Patent
Manteau-Rao et al.

(10) Patent No.: US 11,793,472 B2
(45) Date of Patent: Oct. 24, 2023

(54) SYSTEMS AND METHODS FOR THE TREATMENT OF SYMPTOMS ASSOCIATED WITH MIGRAINES

(71) Applicant: Pear Therapeutics (US), Inc., Boston, MA (US)

(72) Inventors: Marguerite Manteau-Rao, Boston, MA (US); Antoun Nabhan, Boston, MA (US)

(73) Assignee: WELT Corp., Ltd, Seoul (KR)

( * ) Notice: Subject to any disclaimer, the term of this patent is extended or adjusted under 35 U.S.C. 154(b) by 436 days.

(21) Appl. No.: 16/797,385

(22) Filed: Feb. 21, 2020

(65) Prior Publication Data
US 2020/0268324 A1 Aug. 27, 2020

Related U.S. Application Data

(60) Provisional application No. 62/809,251, filed on Feb. 22, 2019.

(51) Int. Cl.
*A61B 5/00* (2006.01)
*G16H 10/60* (2018.01)
(Continued)

(52) U.S. Cl.
CPC ........... *A61B 5/7275* (2013.01); *G16H 10/60* (2018.01); *G16H 20/17* (2018.01); *G16H 20/70* (2018.01);
(Continued)

(58) Field of Classification Search
CPC ....... A61B 5/7275; A61B 5/0004; A61B 5/02; G16H 20/17; G16H 10/60; G16H 20/70; G16H 20/13; A61K 38/225
(Continued)

(56) References Cited

U.S. PATENT DOCUMENTS 7,941,200 B2 * 5/2011 Weinert ................. G16H 40/63
600/347
10,473,955 B2 * 11/2019 McLendon ............ G02C 7/101
(Continued)

FOREIGN PATENT DOCUMENTS

JP 2008237718 A 10/2008
JP 2009521249 A 6/2009
(Continued)

OTHER PUBLICATIONS

International Search Report and Written Opinion for PCT/US2020/019202 dated Jun. 9, 2020.
(Continued)

*Primary Examiner* — Shirley X Jian
(74) *Attorney, Agent, or Firm* — Mark T. Vogelbacker; Eckert Seamans Cherin & Mellott, LLC

(57) ABSTRACT

A method comprising executing a prescription digital therapeutic configured to treat symptoms associated with migraines experienced by a patient. Executing the prescription digital therapeutic comprises: (a) obtaining, by data processing hardware, a plurality of data from (i) first sensors associated with a patient electronic device, (ii) the patient via the patient electronic device, and (iii) a remote server; (b) weighting, by the data processing hardware, the plurality of data to provide a plurality of weighted data; (c) generating, by the data processing hardware, a migraine forecast prediction for the patient based on the plurality of weighted data; (d) determining, by the data processing hardware, a recommended dosage of a migraine-treating medication for the patient based on the migraine forecast prediction, the migraine-treating medication including one of a triptan or a calcitonin gene-related peptide (CGRP) inhibitor; and (e) instructing, by the data processing hardware, an administration unit to administer an administration dosage of the
(Continued)

migraine-treating medication to the patient based on the recommended dosage.

20 Claims, 14 Drawing Sheets

(51) Int. Cl.
    *G16H 20/17*     (2018.01)
    *G16H 20/70*     (2018.01)
    *A61K 38/22*     (2006.01)
    *A61B 5/02*     (2006.01)
    *G16H 20/13*     (2018.01)

(52) U.S. Cl.
    CPC ............ *A61B 5/0004* (2013.01); *A61B 5/02* (2013.01); *A61K 38/225* (2013.01); *G16H 20/13* (2018.01)

(58) Field of Classification Search
    USPC .................................. 600/300–301
    See application file for complete search history.

(56) References Cited

U.S. PATENT DOCUMENTS

| | | | |
|---|---|---|---|
| 2002/0072543 A1* | 6/2002 | Olesen | A61K 31/198 514/565 |
| 2003/0144829 A1* | 7/2003 | Geatz | G16H 10/60 703/22 |
| 2004/0204341 A1* | 10/2004 | Allen | A61P 43/00 514/408 |
| 2015/0151120 A1 | 6/2015 | Saar et al. | |
| 2017/0139233 A1 | 5/2017 | McLendon et al. | |
| 2017/0266106 A1 | 9/2017 | Frangakis et al. | |
| 2018/0052974 A1 | 2/2018 | Madan et al. | |
| 2019/0046123 A1 | 2/2019 | Gago Veiga et al. | |

FOREIGN PATENT DOCUMENTS

| | | |
|---|---|---|
| JP | 2010008825 A | 1/2010 |
| JP | 2016104225 A | 6/2016 |
| JP | 2018531055 A | 10/2018 |
| WO | WO-2016037055 A1 | 3/2016 |
| WO | WO-2018037080 A1 | 3/2018 |

OTHER PUBLICATIONS

Japanese Patent Office. 1st Office Action for Application No. 2021-549518 dated Nov. 14, 2022 (English translation included).
Canadian Patent Office, 1st Examination Report for Application 3130620 dated Oct. 19, 2022.
European Patent Office, Extended Search Report for Application 20758656.1 dated Oct. 6, 2022.
Australian Patent Office, 1st Examination Report for Application 2020225481 dated Sep. 9, 2022.
New Zealand Patent Office, Examination Report for Application No. 780195 dated Mar. 6, 2023.

* cited by examiner

SYSTEMS AND METHODS FOR THE TREATMENT OF SYMPTOMS ASSOCIATED WITH MIGRAINES

CROSS REFERENCE TO RELATED APPLICATIONS

This U.S. patent application claims priority under 35 U.S.C. § 119(e) to U.S. Provisional Application 62/809,251, filed on Feb. 22, 2019. The disclosure of this prior application is considered part of the disclosure of this application and is hereby incorporated by reference in its entirety.

FIELD

The present disclosure relates to digital therapeutics and, more particularly, to systems and methods implementing digital therapeutics for the treatment of symptoms associated with serious medical conditions, such as migraines.

BACKGROUND

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

Drug therapy has played a significant role in the treatment of various medical conditions. Traditional drug therapy involves the administration of pharmaceuticals and the like. Examples of conventional pharmaceuticals may include small-molecule drugs, which are usually derived from chemical synthesis, and biopharmaceuticals, which may include recombinant proteins, vaccines, blood products used therapeutically gene therapy, monoclonal antibodies, cell therapy, and the like.

While drug therapy has proven to be an effective mechanism for treating certain medical conditions, such as migraines, it is not without deficiencies. For example, treatment of a migraine may be limited by reactive systems rather than proactive systems.

Accordingly, systems and methods for improving the treatment of medical conditions, such as migraines, may be desired.

SUMMARY

One aspect of the disclosure provides a system comprising a patient electronic device comprising data processing hardware and memory hardware in communication with the data processing hardware. The memory hardware stores instructions that when executed on the data processing hardware cause the data processing hardware to perform operations comprising executing a prescription digital therapeutic configured to treat symptoms associated with migraines experienced by a patient. Executing the prescription digital therapeutic comprises obtaining a plurality of data from (i) first sensors associated with the patient electronic device, (ii) the patient via the patient electronic device, and (iii) a remote server. Executing the prescription digital therapeutic comprises weighting the plurality of data to provide a plurality of weighted data. Executing the prescription digital therapeutic comprises generating a migraine forecast prediction for the patient based on the plurality of weighted data. Executing the prescription digital therapeutic comprises determining a recommended dosage of a migraine-treating medication for the patient based on the migraine forecast prediction, the migraine-treating medication including one of a triptan or a calcitonin gene-related peptide (CGRP) inhibitor. Executing the prescription digital therapeutic comprises instructing an administration unit to administer an administration dosage of the migraine-treating medication to the patient based on the recommended dosage.

Implementations of the disclosure may include one or more of the following optional features. In some implementations, the system further comprises the administration unit, wherein the administration unit is configured to administer the administration dosage of the migraine-treating medication to the patient based on the instructions. The administration unit may perform operations comprising administering the administration dosage of the migraine-treating medication to the patient.

The prescription digital therapeutic may be configured to implement cognitive behavioral therapy to treat the symptoms associated with migraines.

Executing the prescription digital therapeutic may further comprise obtaining the plurality of data from second sensors associated with the patient, the second sensors comprising one or more of: (i) a heart rate monitor, (ii) a blood pressure monitor, (iii) a sleep monitor, (iv) an electrodermal activity monitor, (v) a skin temperature sensor, and (vi) a sweat monitor.

The first sensors associated with the patient electronic device may comprise one or more of: (i) an accelerometer, (ii) a proximity sensor, (iii) an activity monitor, and (iv) a location system.

The plurality of data obtained from the patient via the input device comprise one or more of: (i) a migraine log, (ii) a migraine intensity indicator, (iii) a successful relief strategy, and (iv) a migraine-treating medication log.

The plurality of data obtained from the remote server may comprise one or more of: (i) a temperature, (ii) a humidity, (iii) a cloud cover, and (iv) a barometric pressure.

Weighting the plurality of data may comprise assigning a first weight to a first data of the plurality of data and a second weight different than the first weight to a second data of the plurality of data.

The administration unit may comprise one or more of: (i) a delivery pump, (ii) an injection unit, (iii) an implant, (iv) an oral absorption unit, (v) an inhaler, and (vi) a nasal injector.

Another aspect of the disclosure provides a method comprising executing a prescription digital therapeutic configured to treat symptoms associated with migraines experienced by a patient. Executing the prescription digital therapeutic comprises obtaining, by data processing hardware, a plurality of data from (i) first sensors associated with a patient electronic device, (ii) the patient via the patient electronic device, and (iii) a remote server. Executing the prescription digital therapeutic comprises weighting, by the data processing hardware, the plurality of data to provide a plurality of weighted data. Executing the prescription digital therapeutic comprises generating, by the data processing hardware, a migraine forecast prediction for the patient based on the plurality of weighted data. Executing the prescription digital therapeutic comprises determining, by the data processing hardware, a recommended dosage of a migraine-treating medication for the patient based on the migraine forecast prediction, the migraine-treating medication including one of a triptan or a calcitonin gene-related peptide (CGRP) inhibitor. Executing the prescription digital therapeutic comprises instructing, by the data processing hardware, an administration unit to administer an administration dosage of the migraine-treating medication to the patient based on the recommended dosage.

Implementations of the disclosure may include one or more of the following optional features. In some implementations, the administration unit is configured to administer the administration dosage of the migraine-treating medication to the patient based on the instructions. Executing the prescription digital therapeutic may further comprise administering, by the administration unit, the administration dosage of the migraine-treating medication to the patient.

The prescription digital therapeutic may be configured to implement cognitive behavioral therapy to treat the symptoms associated with migraines.

Executing the prescription digital therapeutic may further comprise obtaining the plurality of data from second sensors associated with the patient, the second sensors comprising one or more of: (i) a heart rate monitor, (ii) a blood pressure monitor, (iii) a sleep monitor, (iv) an electrodermal activity monitor, (v) a skin temperature sensor, and (vi) a sweat monitor.

The first sensors associated with the patient electronic device may comprise one or more of: (i) an accelerometer, (ii) a proximity sensor, (iii) an activity monitor, and (iv) a location system.

The plurality of data obtained from the patient via the input device may comprise one or more of: (i) a migraine log, (ii) a migraine intensity indicator, (iii) a successful relief strategy, and (iv) a migraine-treating medication log.

The plurality of data obtained from the remote server may comprise one or more of: (i) a temperature, (ii) a humidity, (iii) a cloud cover, and (iv) a barometric pressure.

Weighting the plurality of data may comprise assigning a first weight to a first data of the plurality of data and a second weight different than the first weight to a second data of the plurality of data.

The administration unit may comprise one or more of: (i) a delivery pump, (ii) an injection unit, (iii) an implant, (iv) an oral absorption unit, (v) an inhaler, and (vi) a nasal injector.

The details of one or more implementations of the disclosure are set forth in the accompany drawings and the description below. Other aspects, features, and advantages will be apparent from the description and drawings, and from the claims.

DESCRIPTION OF DRAWINGS

Like reference symbols in the various drawings indicate like elements

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Figure 1:
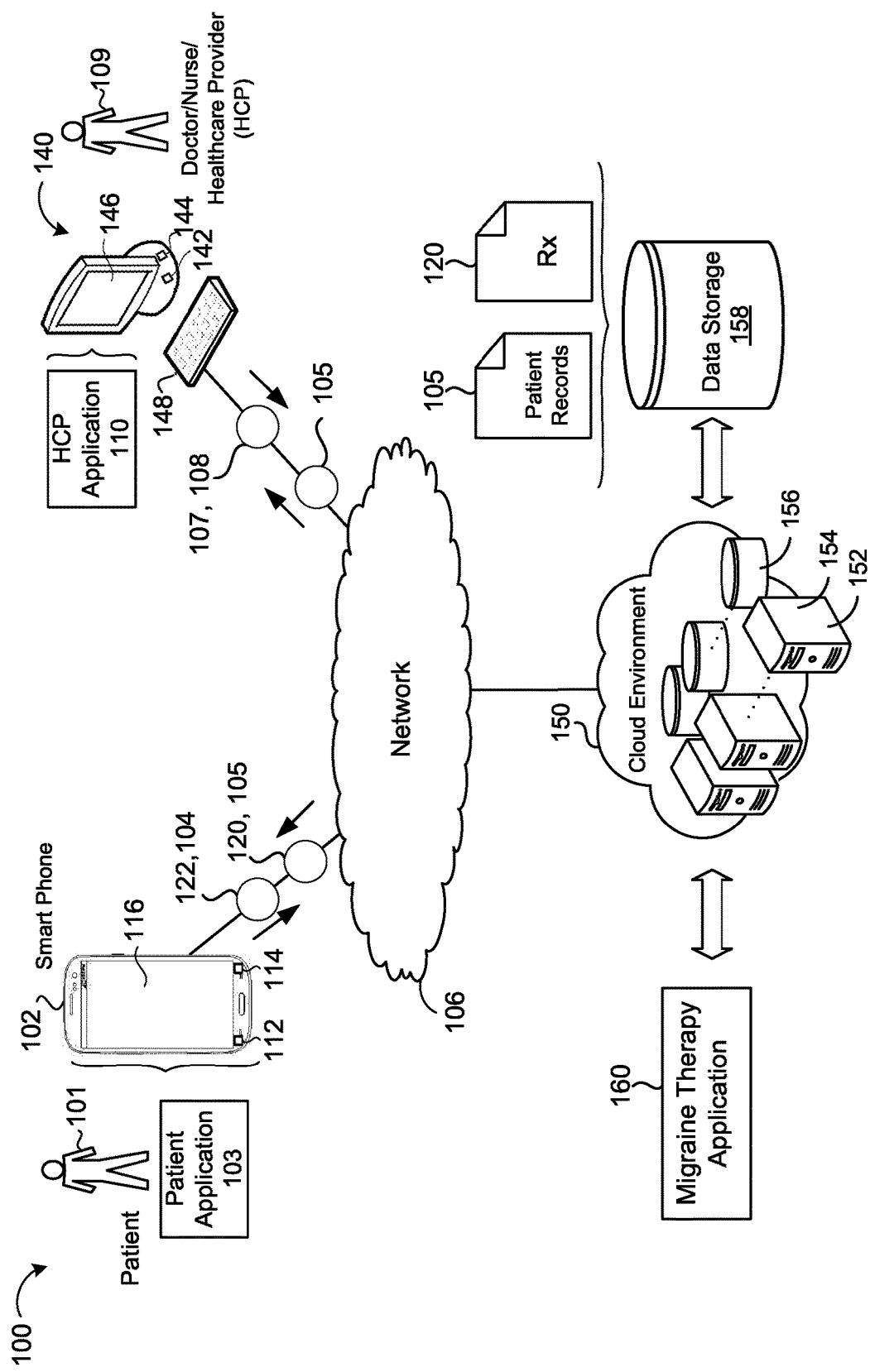
FIG. 1 is a schematic view of a system for treating symptoms associated with migraines including a prescription digital therapeutic in accordance with an exemplary embodiment of the present disclosure.

Referring to FIG. 1, in some implementations, a therapy prescription system 100 provides a patient 101 access to a prescription digital therapeutic 120 prescribed to the patient 101 and monitors events associated with the patient's 101 interaction with the prescription digital therapeutic 120. Although the digital therapeutic 120 is described herein as being a "prescription" digital therapeutic, it is understood that, according to some implementations, the digital therapeutic 120 will not require a prescription from a clinician. Rather, in such implementations, the digital therapeutic 120 may be available to a patient without a prescription, and the digital therapeutic 120 nonetheless otherwise functions in accordance with the description of the prescription digital therapeutic 120 described herein. According to implementations in which the digital therapeutic 120 is not prescribed, the person using or being administered the digital therapeutic may be referred to as a "user." A "user" may include a patient 101 or any other person using or being administered the digital therapeutic 120, irrespective of whether the digital therapeutic 120 was prescribed to that person.

As used herein, a digital therapy may also be referred to as a digital-therapeutic configured to deliver evidence-based psychosocial intervention techniques for treating a patient with a particular disease or disorder, as well as symptoms and/or behaviors associated with the particular disease or disorder, such as migraines. As one example, the patient 101 may experience chronic migraines and the prescription digital therapeutic 120 may be specifically tailored for addressing one or more symptoms associated with the chronic migraines that the patient 101 may experience. In some implementations, the digital therapeutic 120 may include or be combined with traditional drug therapy (e.g., a triptan(s), such as almotriptan, eletriptan, frovatriptan, naratriptan, rizatriptan, sumatriptan, and zolmitriptan, a triptan(s) combined with a nonsteroidal anti-inflammatory drug(s) (NSAID) such as naproxen, aspirin, and ibuprofen, a calcitonin gene-related peptide (CGRP) inhibitor(s) such as eptinezumab, erenumab, fremanezumab, and galcanezumab, any combination of the foregoing, etc.), which similarly may or may not require a prescription. An authorized healthcare provider (HCP) 109 (e.g., a doctor, nurse, etc.) may prescribe the patient 101 the prescription digital therapeutic 120 designed to treat symptoms in the patient 101. The HCP 109 may include a physician, nurse, clinician, or other qualified health professionals. The HCP 109 may provide any suitable level of supervision to the patient 101, including little to no supervision.

In some examples, the system 100 includes a network 106, a patient device 102, an HCP system 140, and a migraine therapy application 160. The network 106 provides access to cloud computing resources 150 (e.g., distributed system) that execute the migraine therapy application 160 to provide for the performance of services on remote devices. Accordingly, the network 106 allows for interaction between patients 101 and HCPs 109 with the migraine therapy application 160. For instance, the migraine therapy application 160 may provide the patient 101 access to the prescription digital therapeutic 120 and receive user input or event data 122 inputted by the patient 101 associated with the patient's 101 interaction with the prescription digital therapeutic 120. In turn, the migraine therapy application 160 may store the event data 122 on a storage resource 156.

The network 106 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, fifth generation (5G) network, a satellite communications network, and other communication networks. The network 106 may include one or more of a Wide Area Network (WAN), a Local Area Network (LAN), and a Personal Area Network (PAN). In some examples, the network 106 includes a combination of data networks, telecommunication networks, and a combination of data and telecommunication networks. The patient device 102, the HCP system 140, and the migraine therapy application 160 communicate with each other by sending and receiving signals (wired or wireless) via the network 106, which, in some examples, may utilize Bluetooth, Wi-Fi, etc. In some examples, the network 106 provides access to cloud computing resources, which may be elastic/on-demand computing and/or storage resources 156 available over the network 106. The term "cloud" services generally refers to a service delivered from one or more remote devices accessible via one or more networks 106, rather than a service performed locally on a user's device.

Figure 2:
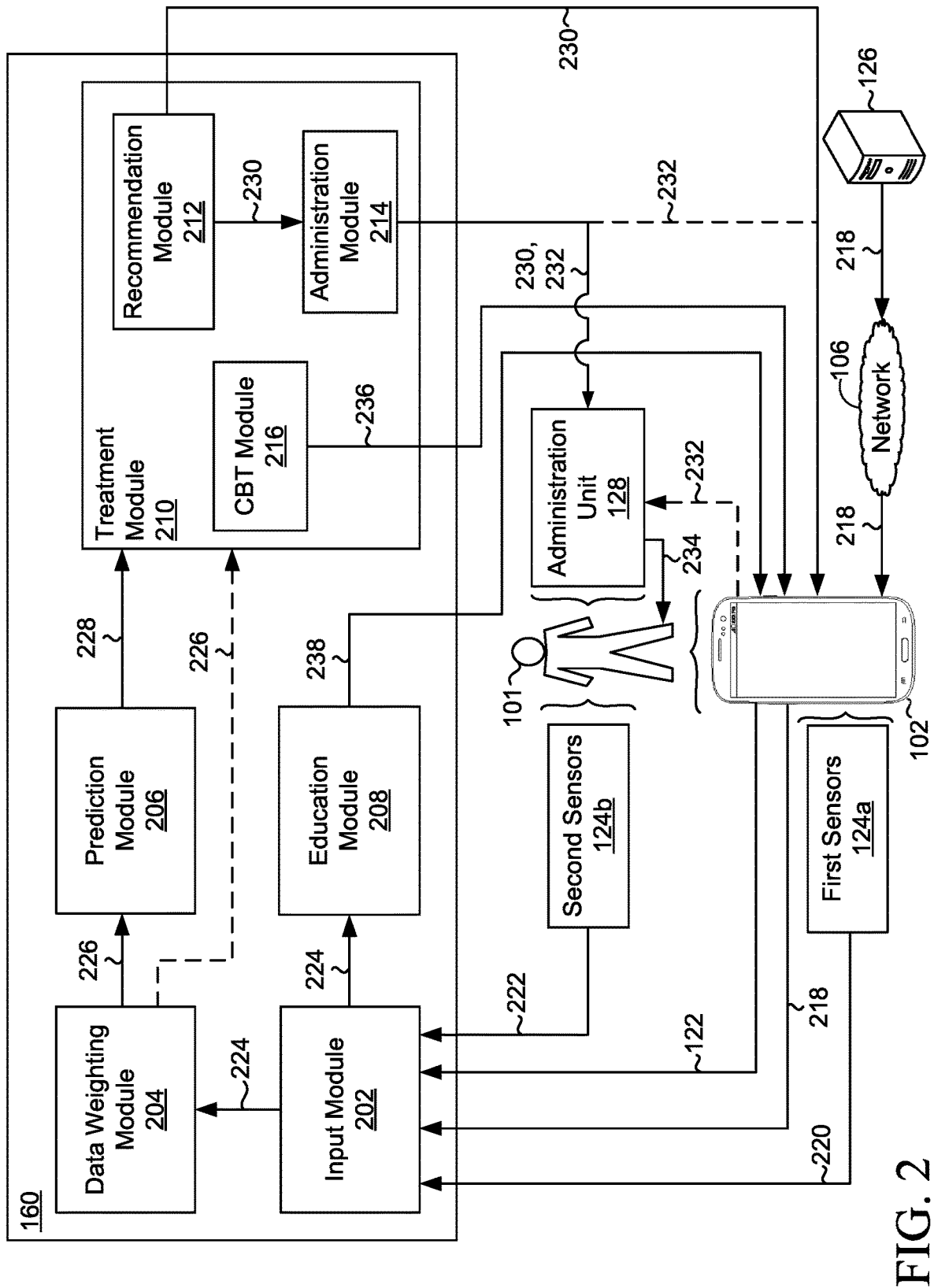
FIG. 2 is a schematic view of a system for treating symptoms associated with migraines using the prescription digital therapeutic of FIG. 1.

The patient device 102 may include, but is not limited to, a portable electronic device (e.g., smartphone, cellular phone, personal digital assistant, laptop computer, or wireless tablet device), a desktop computer, or any other electronic device capable of sending and receiving information via the network 106. The patient device 102 includes data processing hardware 112 (a computing device that executes instructions), memory hardware 114, a display 116, and an input device (not shown) in communication with the data processing hardware 112. Referring to FIGS. 1 and 2, in some implementations, the patient device may include first sensor(s) 124a, such as an accelerometer, proximity sensor, an activity or exercise monitor, location sensors such as a global positioning system (GPS), etc., to provide data about the patient 101 and/or the patient's 101 interaction with the patient device 102. Additionally, or alternatively, the patient 101 may be connected to second sensor(s) 124b, such as a heart rate sensor or monitor, blood pressure sensor or monitor, a sleep sensor, an activity monitor (e.g., an electrodermal activity monitor), a skin temperature sensor, a sweat monitor, and/or any other suitable sensors or monitors (e.g., wearable sensors or monitors) in communication with the patient device 102. In some implementations, the patient 101 and the patient device 102 may be in communication with an administration unit 128, such as a delivery pump, an injection unit, an implant, an oral absorption unit (e.g., a sublingually dissolvable film or pill), an inhaler, a nasal injector, other transmucosal administration units, etc. For example, the patient device 102 may transmit a recommendation and/or an instruction to the administration unit 128 for a dosage of medication the patient 101 should take. In some examples, the patient device 102 includes the input device, e.g., a keyboard, mouse, microphones, touch sensor behind the display 116, and/or a camera for allowing the patient 101 to input data. In addition to or in lieu of the display 116, the patient device 102 may include one or more speakers to output audio data to the patient 101. For instance, audible alerts may be output by the speaker to notify the patient 101 about some time sensitive event associated with the prescription digital therapeutic 120.

In some implementations, the patient device 102 executes the patient application 103 (or accesses a web-based patient application) for establishing a connection with the migraine therapy application 160 to access the prescription digital therapeutic 120. For instance, the patient 101 may have access to the patient application 103 for a duration (e.g., 3 months) of the prescription digital therapeutic 120 prescribed to the patient 101. Here, the patient device 102 may launch the patient application 103 by initially providing an access code 104 when the prescription digital therapeutic 120 is prescribed by the HCP 109, the access code 104 allowing the patient 101 to access content associated with the prescription digital therapeutic 120 from the migraine therapy application 160. The content may be specifically tailored for treating/addressing one or more symptoms associated with the specific indication that the patient 101 may be experiencing, e.g., migraines. The patient application 103, when executing on the data processing hardware 112 of the patient device 102, is configured to display a variety of graphical user interfaces (GUIs) on the display 116 of the patient device 102 that, among other things, allow the patient 101 to (i) input event data 122 describing one or more parameters associated with the patient 101 (e.g., an indication of how the patient 101 is feeling (e.g., experiencing stress, menstruation, fatigue, sleep-deprivation, etc.), an indication of a time the patient 101 experienced a migraine, an indication of where the patient 101 was located when they experienced a migraine, an indication of who the patient 101 was with when they experienced a migraine, an indication of the time of day the patient 101 experienced a migraine, etc.); (ii) solicit information from the patient 101; (iii) deliver therapeutic content (e.g., cognitive behavioral therapy (CBT) content) to the patient 101; (iv) allow the patient 101 to contact their HCP 109; (v) allow the patient 101 to review their progress adhering to their prescription regimen with respect to the prescription digital therapeutic 120 and/or any prescribed medication; and/or (vi) present journal entries for the patient 101 to view and/or edit.

The storage resources 156 may provide data storage 158 for storing the event data 122 received from the patient 101 in a corresponding patient record 105 as well as the prescription digital therapeutic 120 prescribed to the patient 101. The patient record 105 may be encrypted while stored on the data storage 158 so that any information identifying patient 101 is anonymized, but may later be decrypted when the patient 101 or supervising HCP 109 requests the patient record 105 (assuming the requester is authorized/authenticated to access the patient record 105). All data transmitted over the network 106 between the patient device 102 and the cloud computing system 150 may be encrypted and sent over secure communication channels. For instance, the patient application 103 may encrypt the event data 122 before transmitting to the migraine therapy application 160 via the HTTPS protocol and decrypt a patient record 105 received from the migraine therapy application 160. When network connectivity is not available, the patient application 103 may store the event data 122 in an encrypted queue within the memory hardware 114 until network connectivity is available.

The HCP system 140 may be located at a clinic, doctor's office, or facility administered by the HCP 109 and includes data processing hardware 142, memory hardware 144, and a display 146. The memory hardware 144 and the display 146 are in communication with the data processing hardware 142. For instance, the data processing hardware 142 may reside on a desktop computer or portable electronic device for allowing the HCP 109 to input and retrieve data to and from the migraine therapy application 160. In some examples, the HCP 109 may initially onboard some or all of patient data 107 at the time of prescribing the prescription digital therapeutic 120 to the patient 101. The HCP system 140 includes a keyboard 148, mouse, microphones, speakers and/or a camera.

In some implementations, the HCP system 140 (i.e., via the data processing hardware 142) executes the HCP application 110 (or accesses a web-based patient application) for establishing a connection with the migraine therapy application 160 to input and retrieve data therefrom. For instance, the HCP system 140 may be able to access the anonymized patient record 105 securely stored by the migraine therapy application 160 on the storage resources 156 by providing an authentication token 108 validating that the HCP 109 is supervising the patient 101 and authorized to access the corresponding patient record 105. The authentication token 108 may identify the particular patient 101 associated with the patient record 105 that the HCP system 140 is permitted to obtain from the migraine therapy application 160. The patient record 105 may include time-stamped event data 122 indicating the patient's interaction with the prescription digital therapeutic 120 through the patient application 103 executing on the patient device 102. The HCP application 110, when executing on the data processing hardware 142 of the HCP system 140, is configured to display a variety of graphical user interfaces (GUIs) on the display 146 of the HCP system 140 that, among other things, allow the HCP 109 to input event data 122 describing one or more parameters associated with the patient 101, solicit information from the patient 101, and input clinical notes associated with the patient 101.

In some implementations, the HCP application 110 is in communication with a single patient application 103 for a single patient 101 and manages data associated with the single patient application 103. In other implementations, the HCP application 110 is in communication with several patient applications 103 associated with several patients 101, and the HCP application 110 may manage and display the data associated with the several patient applications 103 in any suitable manner, e.g., by toggling between different views and/or displaying certain data simultaneously. In other implementations, the HCP application 110 is in communication with multiple patient applications 103 for the same patient 101 and simultaneously manages data associated with the multiple patient applications 103. In this implementation, the data from multiple patient applications 103 may be displayed simultaneously in any suitable manner or the data from each patient application 103 may be displayed discretely such that the HCP 109 is able to toggle between the discretely displayed data.

The cloud computing resources 150 may be a distributed system (e.g., remote environment) having scalable/elastic resources 152. The resources 152 include computing resources 154 (e.g., data processing hardware) and/or the storage resources 156 (e.g., memory hardware). The cloud computing resources 150 execute the migraine therapy application 160 for facilitating communications with the patient device 102 and the HCP system 140 and storing data on the storage resources 156 within the data storage 158. In some examples, the migraine therapy application 160 and the data storage 158 reside on a standalone computing device. The migraine therapy application 160 may provide the patient 101 with the patient application 103 (e.g., a mobile application, a web-site application, or a downloadable program that includes a set of instructions) executable on the data processing hardware 112 and accessible through the network 106 via the patient device 102 when the patient 101 provides a valid access code 104. Similarly, the migraine therapy application 160 may provide the HCP 109 with the HCP application 110 (e.g., a mobile application, a web-site application, or a downloadable program that includes a set of instructions) executable on the data processing hardware 142 and accessible through the network 106 via the HCP system 140.

Referring to FIG. 2, the migraine therapy application 160 may include an input module 202, a data weighting module 204, a prediction module 206, an education module 208, and a treatment module 210 having a recommendation module 212, an administration module 214, and a cognitive behavioral therapy (CBT) module 216. It should be understood that fewer or greater modules may be implemented, and certain modules may be combined or separated as suitable. As set forth above, the migraine therapy application 160 may be executed by the cloud computing resources 150 and may be in communication with the patient device 102 associated with the patient 101 via the network 106.

The migraine therapy application 160 is configured to provide educational content and therapeutic content to the patient 101 via the electronic device 102 and migraine-treating medication, such as a triptan or a CGRP inhibitor, which may be administered via the administration unit 128. Additional features and functionality of the migraine therapy application 160 are described in more detail below.

The input module 202 is configured to obtain (e.g., fetch or receive) one or more inputs including event data 122 from the storage resource 156 of the patient device 102, first sensor data 220 from the first sensor(s) 124a associated with the patient device 102, second sensor data 222 from the second sensor(s) 124b associated with or connected to the patient 101, external data 218 from a remote server 126 or the patient device 102 in communication with the remote server 126, etc. In some examples, the input module 202 may actively monitor and gather data from the patient device 102 and/or the sensors 124a, 124b. In other examples, the input module 202 may query the patient 101 to provide information or data from the patient device 102 and/or sensors 124a, 124b.

The patient device 102 is configured to obtain the external data 218 from the remote server 126 in communication with the patient device 102 via the network 106. In some implementations, the input module 202 may obtain the external data 218 directly from the remote server 126 via the network 106. The external data 218 may be related to environmental data, such as temperature, humidity, cloud cover, barometric pressure, etc. The external data 218 may leverage location information (e.g., obtained by GPS on the patient device 102) to determine the environmental data for that particular location of the patient device 102. Additional or alternative external data 218 is contemplated, including news, social media information, etc. The input module 202 is configured to transmit data to, and be in communication with, the data weighting module 204 and the education module 208.

The data weighting module 204 is configured to receive input data 224 from the input module 202. Based on the input data 224, the data weighting module 204 is configured to assign a weight or value to each of the one or more inputs to generate weighted input data 226. For example, the first sensor(s) 124a may include an activity monitor and the first sensor data 220 may include activity data associated with the patient 101. In such an example, the data weighting module 204 may assign a different (e.g., greater or lesser) value to the activity data than, for example, event data 122 inputted by the patient 101. The data weighting module 204 may interpret the input data 224 to determine a current state of the patient 101. For example, the data weighting module 204 may interpret the second sensor data 222 to determine that the patient 101 is currently experiencing menstruation, stress, fatigue, sleep-deprivation, etc. As another example, the data weighting module 204 may interpret the event data 122 to determine that the patient 101 is currently experiencing menstruation, stress, fatigue, sleep-deprivation, etc. The data weighting module 204 is configured to be in communication with and transmit the weighted input data 226 to the prediction module 206.

The prediction module 206 is configured to receive the weighted input data 226 from the data weighting module 204. The prediction module 206 is configured to generate a migraine forecast prediction 228 for the patient 101 based on the weighted input data 226. The migraine forecast prediction 228 may be updated in real-time (or substantially real-time) based on the weighted input data 226. The prediction module 206 may determine the migraine forecast prediction 228 based on the weighted input data 226, which may provide historical data related to the patient 101. The prediction module 206 may implement supervised or unsupervised machine learning or other artificial intelligence to determine the migraine forecast prediction 228. For example, based on the event data 122 and the external data 218, the prediction module 206 may determine that the patient 101 historically records (via the event data 122) a migraine during a specific weather condition (based on the external data 218), e.g., high barometric pressure. Continuing with the example, if the external data 218 indicates that there is high barometric pressure for that particular day, the data weighting module 204 may assign a greater weight to this external data 218, which may affect the prediction module's 206 generation of the migraine forecast prediction 228. The patient 101 and/or the HCP 109 may train the machine learning or other artificial intelligence, e.g., by confirming or denying the existence of a migraine when the migraine forecast prediction 228 indicates a high likelihood of a migraine. The foregoing example applies similarly to other external data 218, such as temperature, humidity, cloud cover, etc., and other data obtained by the input module 202, such as the event data 122, the first sensor data 220, the second sensor data 222, etc. The prediction module 206 is configured to be in communication with and transmit the migraine forecast prediction 228 to the treatment module 210.

The treatment module 210 is configured to receive the migraine forecast prediction 228 from the prediction module 206. In some implementations, the treatment module 210 may be configured to additionally receive the weighted input data 226 from the data weighting module 204. The recommendation module 212 of the treatment module 210 is configured to determine a recommended dosage for the patient 101 based on the migraine forecast prediction 228 and/or the weighted input data 226. The recommendation module 212 may implement supervised or unsupervised machine learning or other artificial intelligence to determine the recommended dosage, e.g., based on an individual patient's medication use patterns during migraine episodes. The patient 101 and/or the HCP 109 may train the machine learning or other artificial intelligence, e.g., by confirming, denying, or modifying the recommended dosage. In the examples described herein, the recommended dosage pertains to one or more dosages of migraine-treating medication designed to treat symptoms associated with migraines, however, it should be understood that the recommended dosage may pertain to any suitable medication for any suitable disease or disorder. The migraine-treating medication may be a triptan(s), such as almotriptan, eletriptan, frovatriptan, naratriptan, rizatriptan, sumatriptan, and zolmitriptan, a triptan(s) combined with a nonsteroidal anti-inflammatory drug(s) (NSAID) such as naproxen, aspirin, and ibuprofen, a calcitonin gene-related peptide (CGRP) inhibitor(s) such as eptinezumab, erenumab, fremanezumab, and galcanezumab, any combination of the foregoing, etc.

The recommendation module 212 is configured to transmit recommended dosage data 230 associated with the recommended dosage to the administration module 214. The recommendation module 212 is also configured to transmit, via the network 106, the recommended dosage data 230 to the patient device 102, causing the patient device 102 to display the recommended dosage on the display 116 in the patient application 103. In some implementations, the recommendation module 212 is configured to automatically transmit the recommended dosage data 230 to the patient device 102 at predetermined intervals (e.g., every 8 hours), or the recommendation module 212 is configured to transmit the recommended dosage data 230 in response to event data 122 inputted by the patient 101 on the patient device 102.

In some implementations, the patient 101 may be associated with the administration unit 128, which, as set forth above, may include, for example, a delivery pump, an injection unit, an implant, an oral absorption unit (e.g., a sublingually dissolvable film or pill), an inhaler, a nasal injector, other transmucosal administration units, etc. The administration unit 128 may be in communication with the administration module 214. The administration module 214 is configured to transmit dosage instruction data 232 and/or the recommended dosage data 230 to the administration unit 128. In some implementations, the administration module 214 is configured to transmit the dosage instruction data 232 to the administration unit 128, which causes the administration unit 128 to administer or deliver an administration dosage 234 based on the recommended dosage to the patient 101. In such implementations, the administration unit 128 may automatically administer or deliver the administration dosage 234 to the patient 101, or the administration unit 128 may query the patient 101 and/or the HCP 109 to confirm the recommended dosage before administering the administration dosage 234 to the patient 101. In some implementations, the administration module 214 may be in communication with and configured to transmit the dosage instruction data 232 to the patient device 102 and the patient device 102 may be in communication with and configured to transmit the dosage instruction data 232 to the administration unit 128.

The CBT module 216 is configured to transmit CBT content or data 236 to the patient device 102 based on the migraine forecast prediction 228 and/or the weighted input data 226. The CBT data 236 is configured to treat symptoms associated with migraines, such as anxiety, depression, pain, etc. The CBT data 236 may be displayed or presented on the patient device 102 in any suitable form, such as, an audio presentation, a video presentation, an audio/visual presentation, a textual presentation, an interactive display, etc. In some implementations, the CBT module 216 is pre-programmed with a plurality of CBT techniques. In other implementations, the CBT module 216 may obtain a plurality of CBT techniques from an external source (e.g., a remote server) via the network 106.

The treatment module 210 may determine which therapeutic content (i.e., recommended dosage data 230, the dosage instruction data 232, and the CBT data 236) to deliver to the patient device 102 and/or the administration unit 128 based on the migraine forecast prediction 228 and/or the weighted input data 226. As set forth above with respect to the prediction module 206, this determination by the treatment module 210 may be based at least in part on historical data associated with the patient 101, including implementing supervised or unsupervised machine learning or other artificial intelligence. Additionally or alternatively, the patient 101 (via interaction with the patient device 102) or the HCP 109 may determine which therapeutic content is delivered.

The education module 208 is configured to receive the input data 224 from the input module 202. Based on the input data 224, the education module 208 is configured to transmit educational content or data 238 to the patient device 102. The educational data 238 is designed to inform the patient 101 about migraines and the symptoms associated with migraines. The educational data 238 may be tailored to address the current symptoms experienced by the patient 101 based on the input data 224 and/or the educational data 238 may be accessible via the patient device 102 in a catalogued manner. Similarly, the educational data 238 may be pushed to the patient device 102 in response to a certain event (e.g., the patient 101 indicating that they are experiencing a migraine) and/or the educational data 238 may be accessible by the patient 101 via the patient device 102 on their own accord. The educational data 238 may be displayed or presented on the patient device 102 in any suitable form, such as, an audio presentation, a video presentation, an audio/visual presentation, a textual presentation, an interactive display, etc. In some implementations, the education module 208 is pre-programmed with a plurality of educational information. In other implementations, the education module 208 may obtain a plurality of educational information from an external source (e.g., a remote server) via the network 106.

Referring to FIGS. 3A-3I, a plurality of exemplary graphical user interfaces (GUIs) 300*a-i* of the prescription digital therapeutic 120 (e.g., by execution of the patient application 103 and the migraine therapy application 160) displayed on the display 116 of the patient device 102. The example GUIs 300*a-i* are configured to display graphical elements (e.g., buttons) that the patient 101 may select via user inputs such as touch inputs, speech inputs, or other input techniques such as via a mouse, stylus, keyboard, gesture, or eye gaze.

Figure 3A:
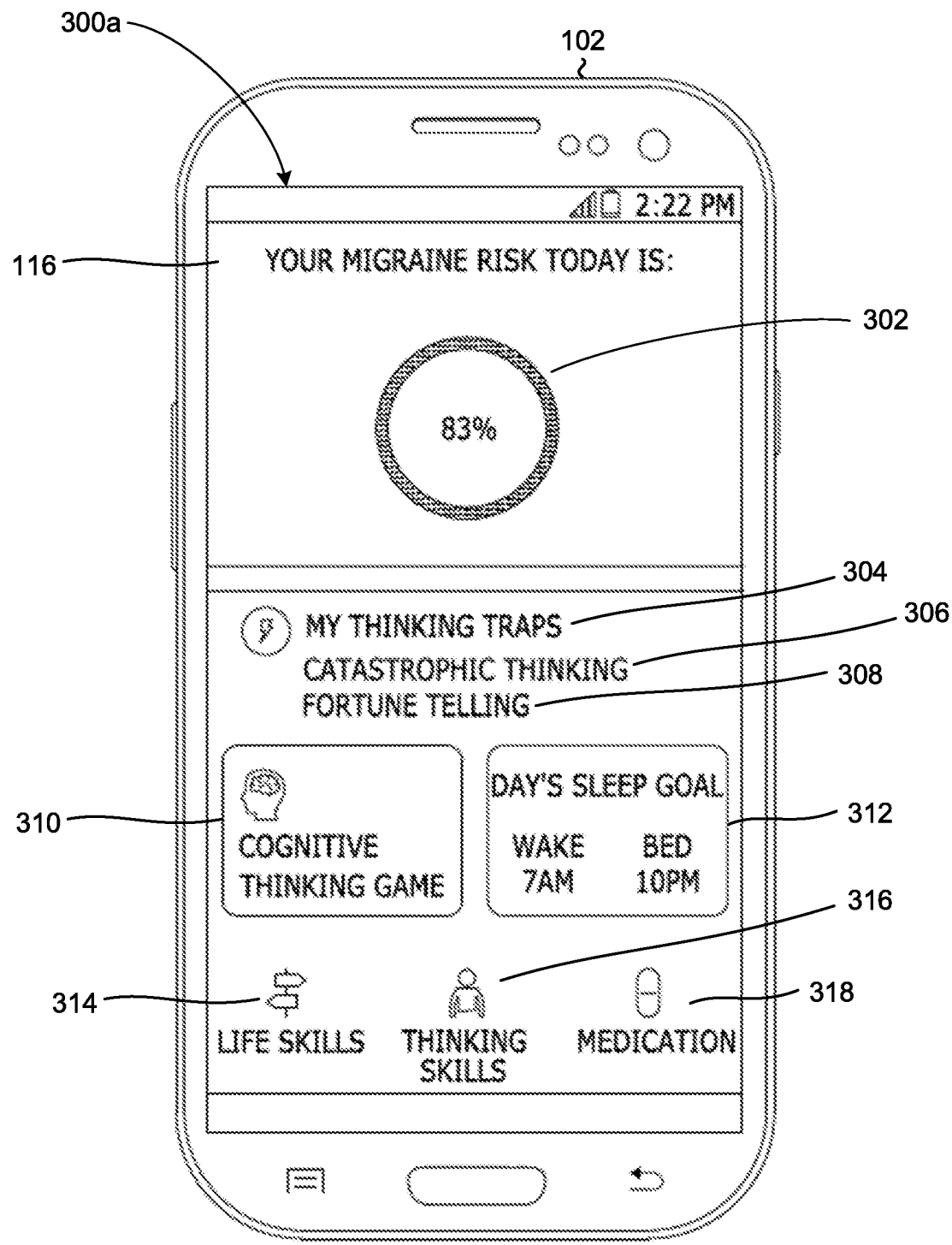
FIGS. 3A-3I are exemplary GUIs of the prescription digital therapeutic of FIG. 1 displayed on a display of a patient electronic device.

Referring to FIG. 3A, in a first implementation, upon launching the patient application 103 associated with the prescription digital therapeutic 120 prescribed to the patient 101, the patient application 103 displays an exemplary first opening GUI 300*a*. The first opening GUI 300*a* provides a migraine forecast prediction interface element 302 based on the migraine forecast prediction 228. For example, the migraine forecast prediction interface element 302 may be illustrated as a percentage indicating the percent chance that the patient 101 experiences a migraine for that particular day or at that particular time. As set forth above, the migraine forecast prediction interface element 302 may update in real-time (or substantially real-time) based on the updates to the migraine forecast prediction 228. Additionally or alternatively, the migraine forecast prediction interface element 302 may be illustrated textually, e.g., "High Chance of Migraine," "Low Chance of Migraine," etc., as shown in FIG. 3B.

In some configurations, the patient application 103 causes the patient device to display a thinking traps interface element 304 that allows the patient 101 to input a thinking trap associated with the particular thoughts they are having. Similarly, a catastrophic thinking interface element 306 and a fortune telling interface element 308 may also be displayed which allow the patient 101 to input a catastrophic thought and a future thought, respectively. It should be noted that while the example shown depicts the thinking traps interface element 304, the catastrophic thinking interface element 306, and the fortune telling interface element 308, in other examples, the first opening GUI 300*a* can display any other type of cognitive distortions.

In some implementations, the first opening GUI 300*a* displays a cognitive thinking game interface element 310 that allows the patient 101 to interact with the patient device 102 in a game environment executed by the CBT module 216. The first opening GUI 300*a* may display a sleep goal interface element 312 which illustrates a target wake-up time and a target sleep time for the patient 101 for that particular day. The sleep goal interface element 312 may be pre-programmed by the patient 101 or the HCP 109, or the sleep goal interface element 312 may be tailored to the patient 101 based on the migraine forecast prediction 228 and/or the weighted input data 226. The first opening GUI 300*a* may display a life skills interface element 314 and a thinking skills interface element 316 executed by one or more of the education module 208 or the CBT module 216. The first opening GUI 300*a* may display a medication interface element 318 corresponding to the recommendation module 212, the administration module 214, and/or the administration unit 128.

Figure 3B:
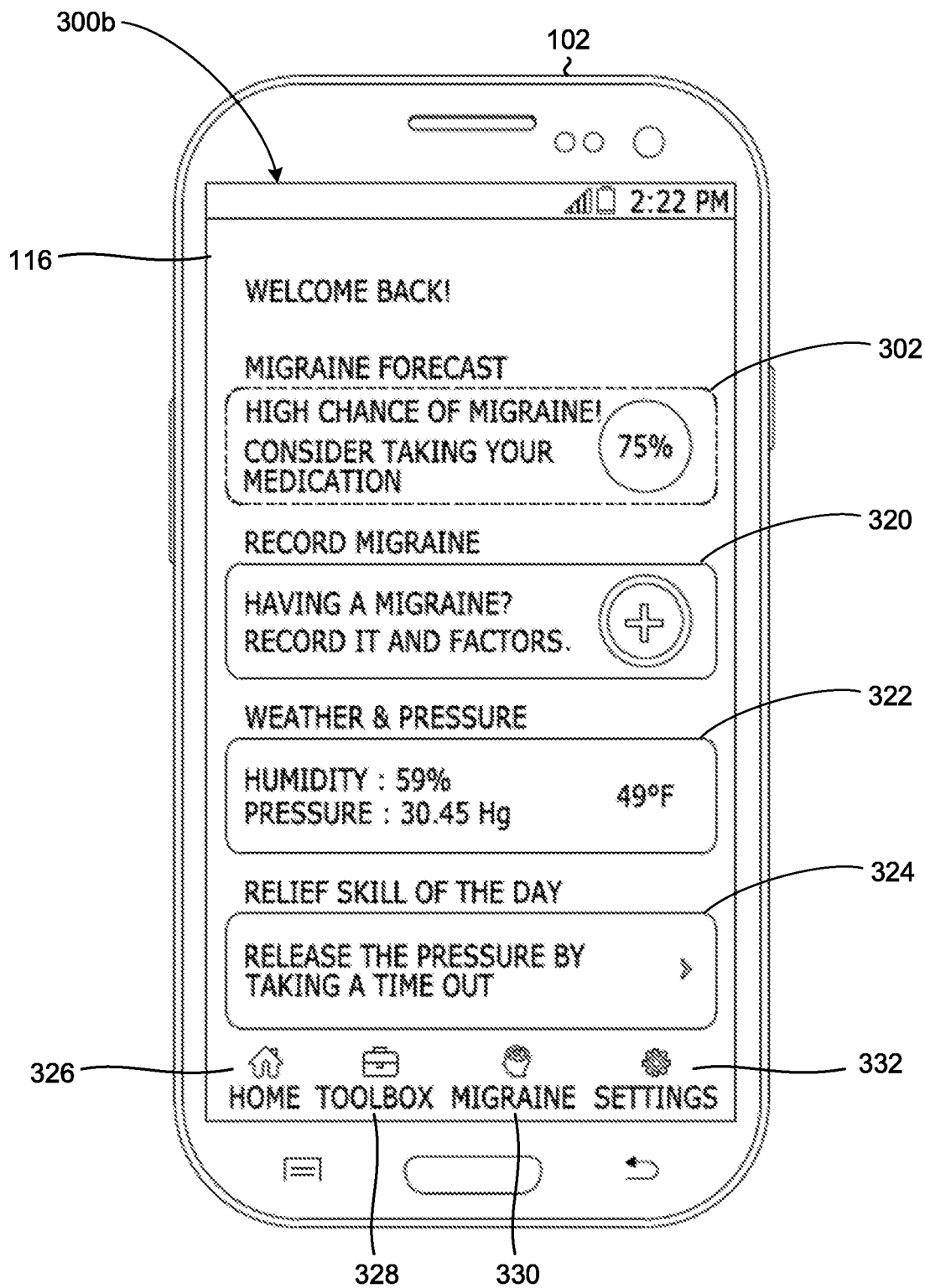

Referring to FIG. 3B, in a second implementation, upon launching the patient application 103 associated with the prescription digital therapeutic 120 prescribed to the patient 101, the patient application 103 displays an exemplary second opening GUI 300*b*. The second opening GUI 300*b* provides the migraine forecast prediction interface element 302 based on the migraine forecast prediction 228. The second opening GUI 300*b* may display a record migraine interface element 320 allowing the patient 101 to record when the patient 101 is experiencing a migraine and factors associated with the migraine. The second opening GUI 300*b* may display an environmental interface element 322 displaying, for example, the external data 218, such as weather and pressure data. In some implementations, the environmental interface element 322 may display other information corresponding to the external data 218. The second opening GUI 300*b* may display a relief skill interface element 324 which may illustrate CBT data 236 executed by the CBT module 216. The second opening GUI 300*b* may display a home interface element 326, a toolbox interface element 328 for accessing CBT content and education materials as shown in FIG. 3H, a migraine interface element 330 for logging migraines, and a settings interface element 332.

Figure 3C:
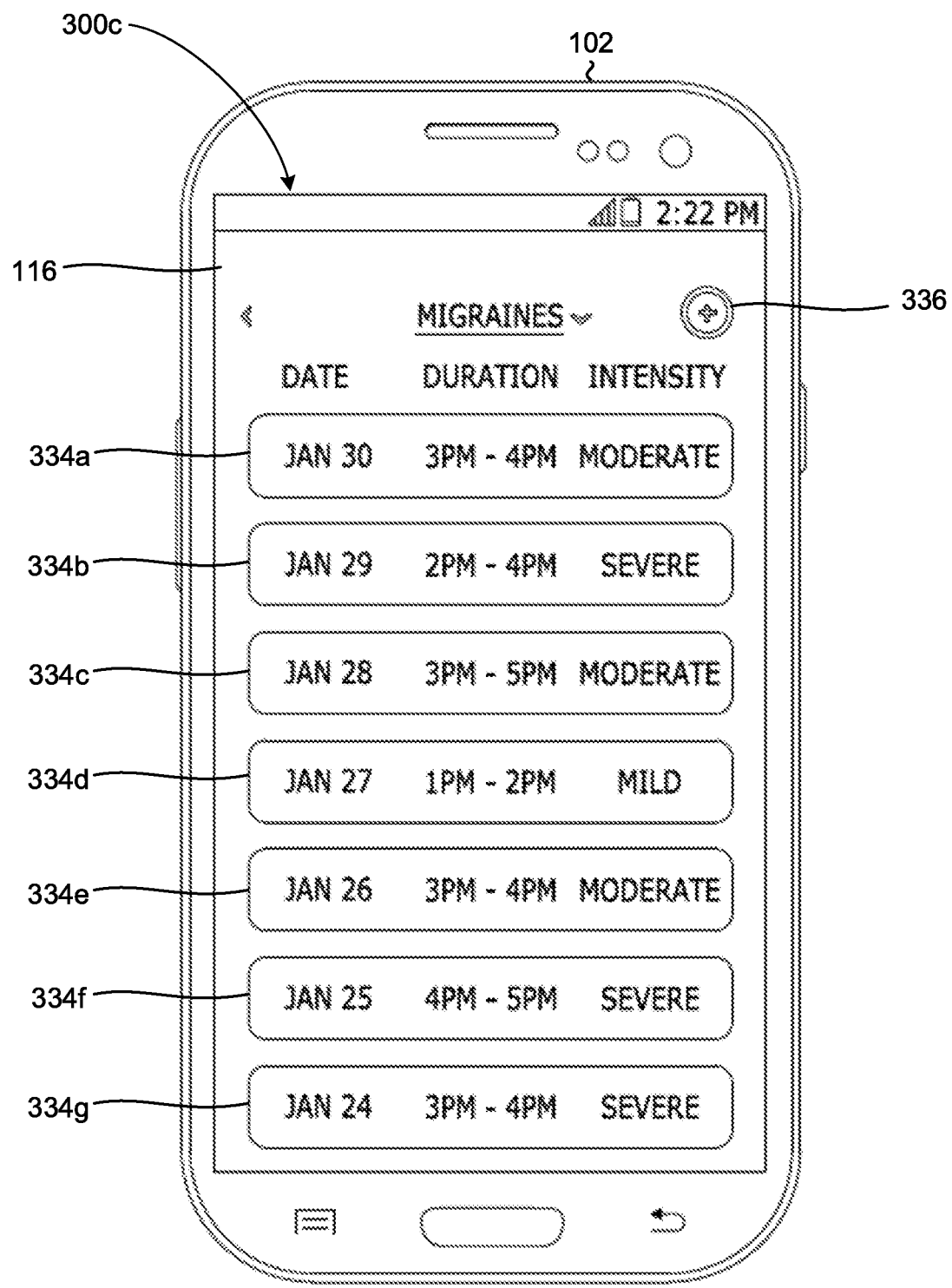

Referring to FIG. 3C, in some implementations, the patient application 103 displays a migraine log GUI 300c. For example, the patient application 103 may display the migraine log GUI 300c in response to the patient device 102 detecting a feeling selection input (e.g., touch or spoken) corresponding to, e.g., the record migraine interface element 320 or the migraine interface element 330. The migraine log GUI 300c displays a plurality of logged migraine interface elements 334a-g, each logged migraine interface element 334a-g indicating a date, duration, and intensity of that specific migraine. As one example, as shown in FIG. 3C, the first logged migraine interface element 334a occurred on January 30, lasted from 3 PM to 4 PM, and had a moderate intensity. The migraine log GUI 300c displays an add migraine interface element 336 which allows the patient 101 to add another migraine to the migraine log.

Figure 3D:
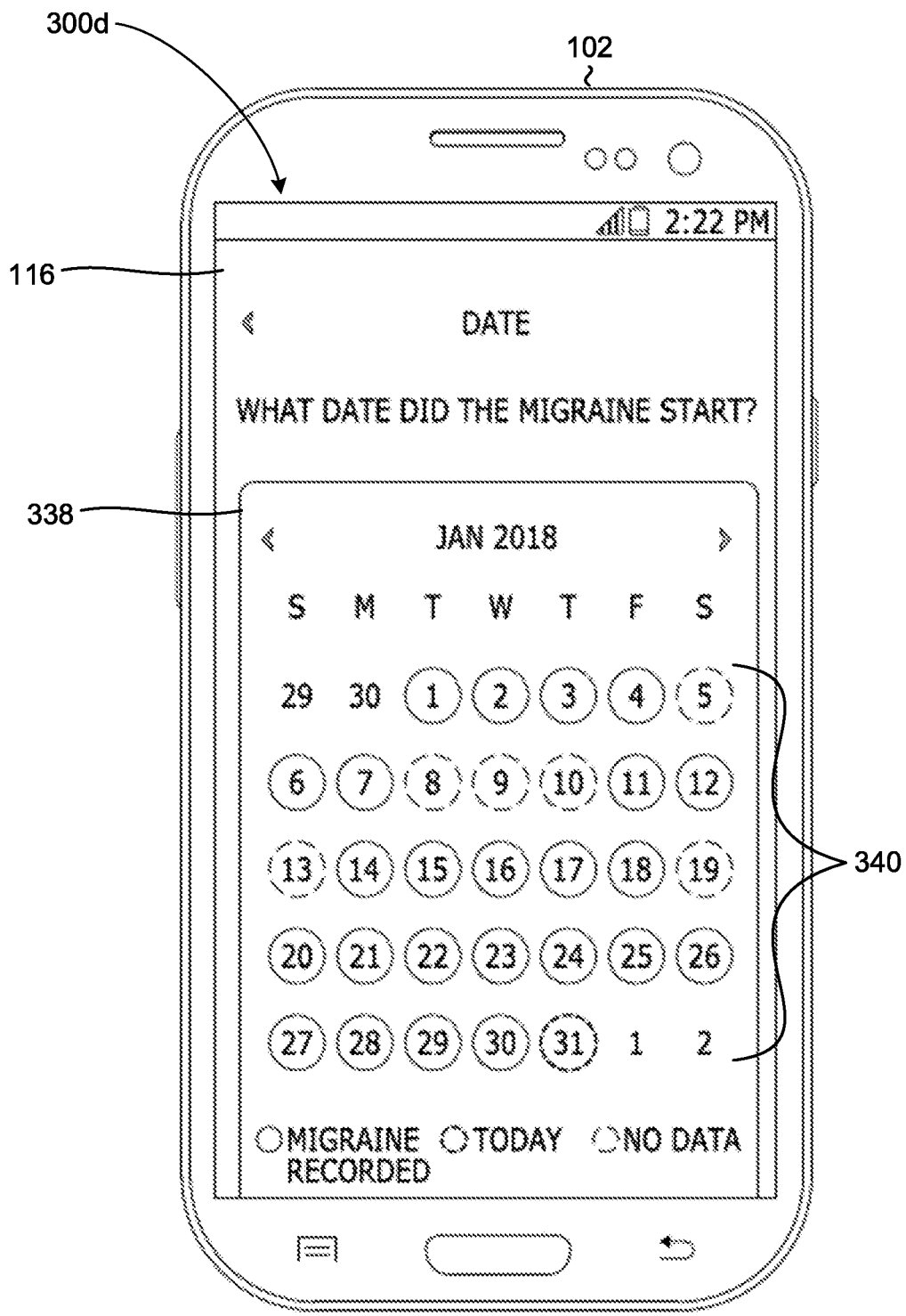

Referring to FIG. 3D, in some implementations, upon the patient device 102 detecting a feeling selection input corresponding to, e.g., the add migraine interface element 336, the patient application 103 displays a migraine date GUI 300d. The migraine date GUI 300d displays a calendar interface element 338 which graphically illustrates a plurality of date interface elements 340 illustrating past migraines corresponding to the logged migraine interface elements 334a-g for each date of a selected month.

Figure 3E:
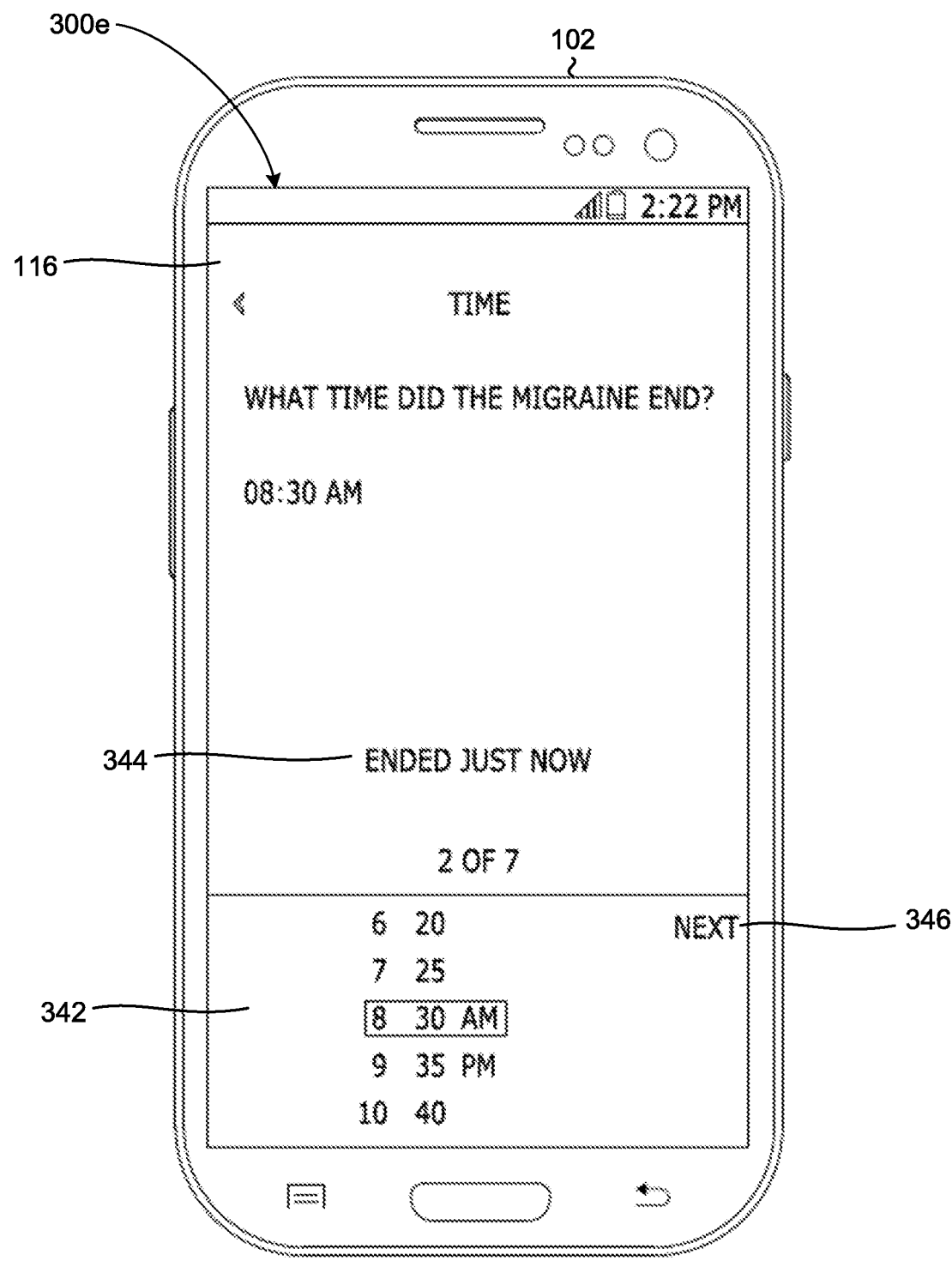

Referring to FIG. 3E, in some implementations, upon the patient device 102 detecting a feeling selection input corresponding to, e.g., one of the plurality of date interface elements 340 of the calendar interface element 338, the patient application 103 displays a migraine time GUI 300e. The migraine time GUI 300e displays a time interface element 342 for identifying when the migraine ended. The migraine time GUI 300e may display an "ended just now" interface element 344 for specifying that the migraine ended at the time the patient device 102 detects a feelings selection input corresponding to the "ended just now" interface element 344. The migraine time GUI 300e may display a next interface element 346.

Figure 3F:
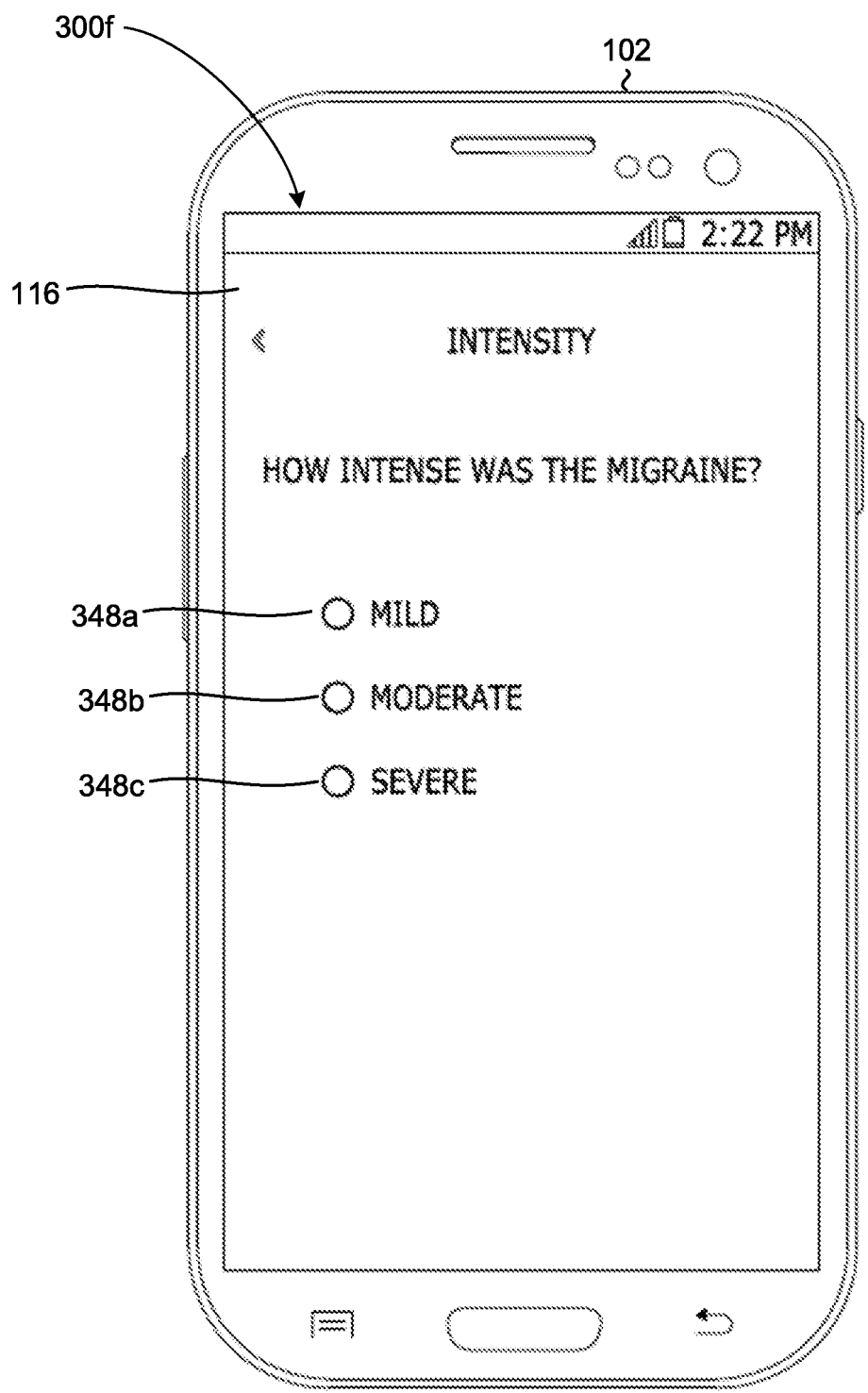

Referring to FIG. 3F, in some implementations, upon the patient device 102 detecting a feeling selection input corresponding to, e.g., the next interface element 346, the patient application 103 displays a migraine intensity GUI 300f. The migraine intensity GUI 300f displays a first migraine intensity interface element 348a corresponding to "mild," a second migraine intensity interface element 348b corresponding to "moderate," and a third migraine intensity interface element 348c corresponding to "severe." Additional or alternative migraine intensity interface elements may be displayed, such as a sliding scale, a color scale, a number scale, etc.

Figure 3G:
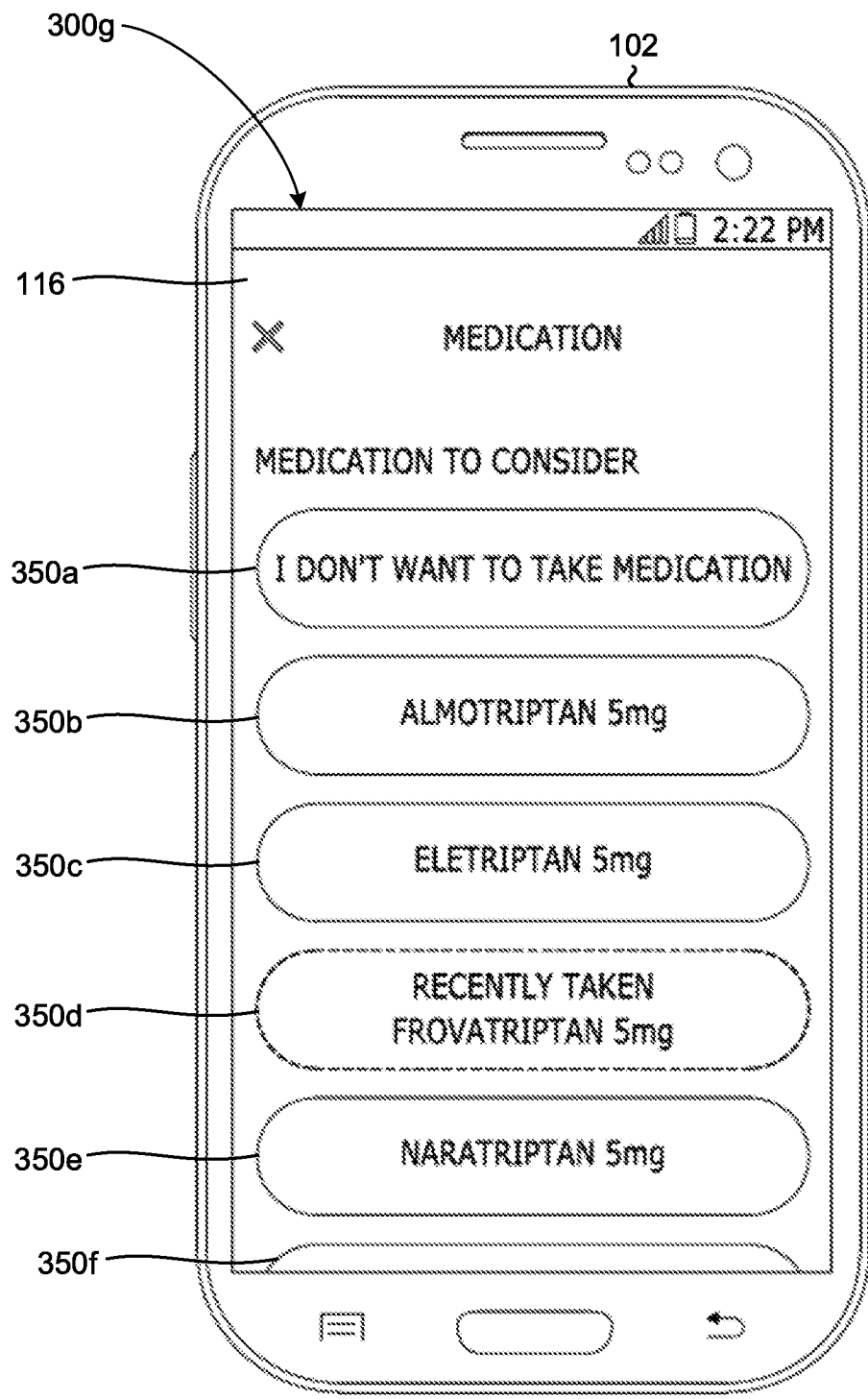
Figure 3H:
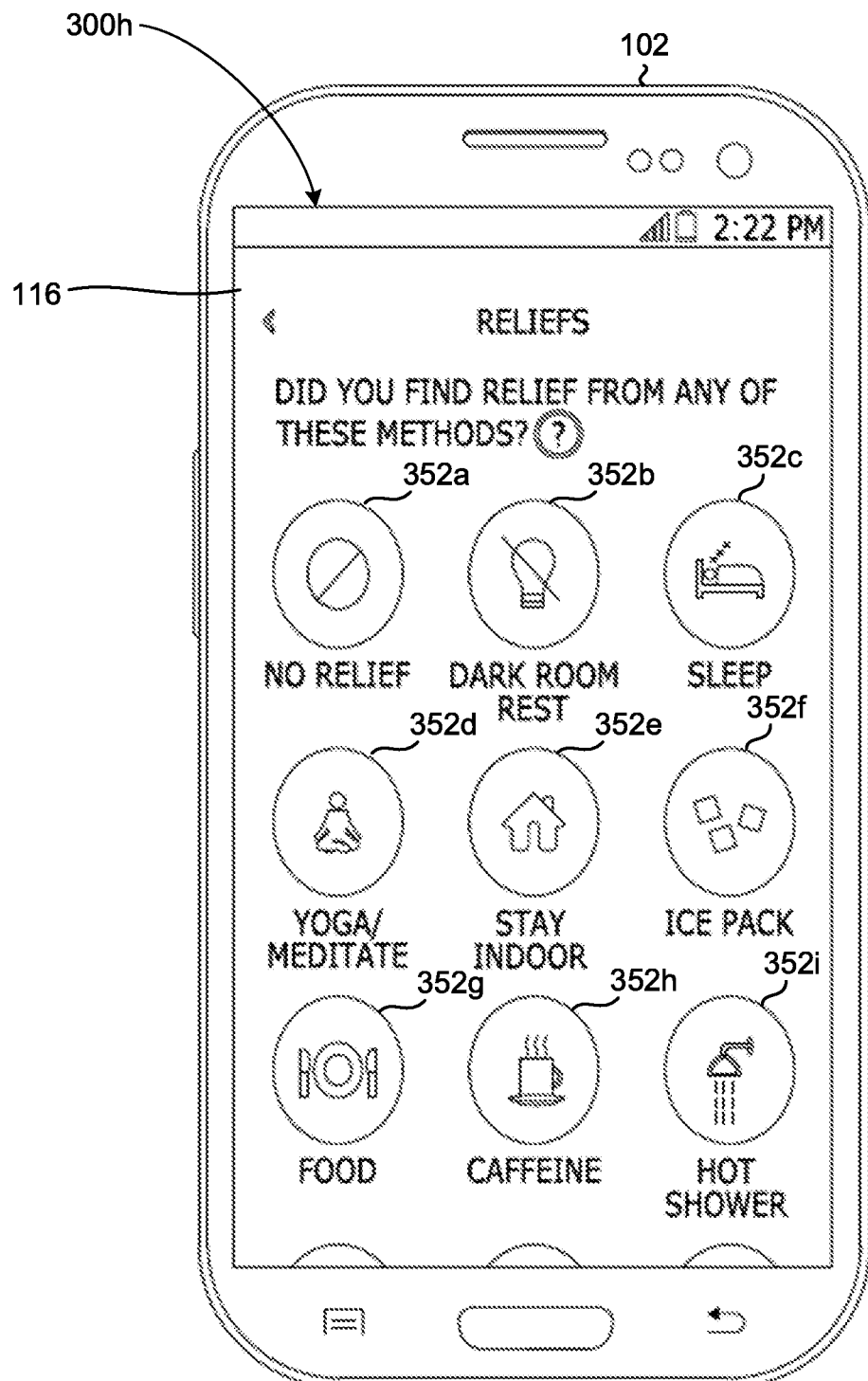

Referring to FIG. 3G, in some implementations, upon the patient device 102 detecting a feeling selection input corresponding to, e.g., the next interface element 346, the patient application 103 displays a medication GUI 300g displaying a plurality of medication interface elements 350a-f. In some implementations, one of the medication interface elements (e.g., the first medication interface element 350a) may correspond to no medication. For example, as shown in FIG. 3G, the first medication interface element 350a may display "I don't want to take medication." The medication GUI 300g may highlight (e.g., by text, change of color, dashed border, etc.) a recently taken medication. For example, as shown in FIG. 3G, the fourth medication interface element 350d is highlighted by text and a dashed border to specify that 5 mg of frovatriptan was recently taken.

Referring to FIG. 3H, in some implementations, upon the patient device 102 detecting a feeling selection input corresponding to, e.g., the relief skill interface element 324, the patient application 103 displays a relief GUI 300h displaying a plurality of relief method interface elements 352a-i. For example, the relief method interface elements 352a-i may correspond to non-pharmacological relief methods, e.g., sleep, yoga, ice pack, etc. Upon the patient device 102 detecting a feeling selection input corresponding one of the plurality of relief method interface elements 352a-i, the prediction module 206 may factor in this selection when generating the migraine forecast prediction 228. For example, if the patient 101 indicates that they found relief from, e.g., the second relief interface method 352b corresponding to dark room rest, then for a future migraine forecast prediction 228, if the patient 101 indicates (via the event data 122) that they have experienced dark room rest, then the prediction module 206 may decrease the likelihood of a migraine as represented by the migraine forecast prediction 228.

Figure 3I:
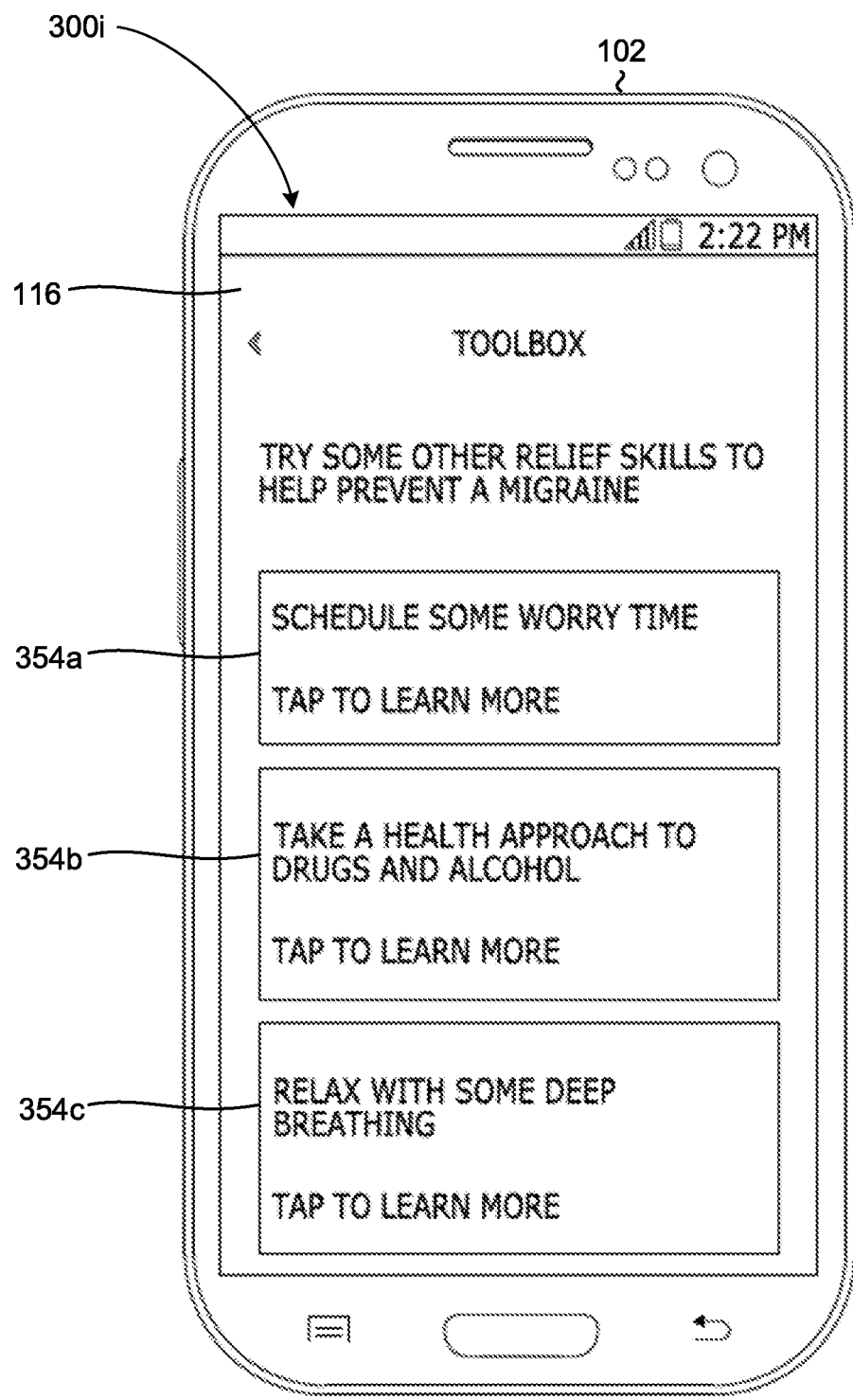

Referring to FIG. 3I, in some implementations, upon the patient device 102 detecting a feeling selection input corresponding to, e.g., the toolbox interface element 328, the patient application 103 displays a toolbox GUI 300i displaying a plurality of other relief skill interface elements 354a-c, e.g., "schedule some worry time," "take a health approach to drugs and alcohol," "relax with some deep breathing," etc. The other relief skill interface elements 354a-c may correspond to CBT data 236 and/or education data 238 executed by the CBT module 216 and the education module 208, respectively. Additionally or alternatively, the toolbox GUI 300i may display any suitable other relief skills.

Figure 4:
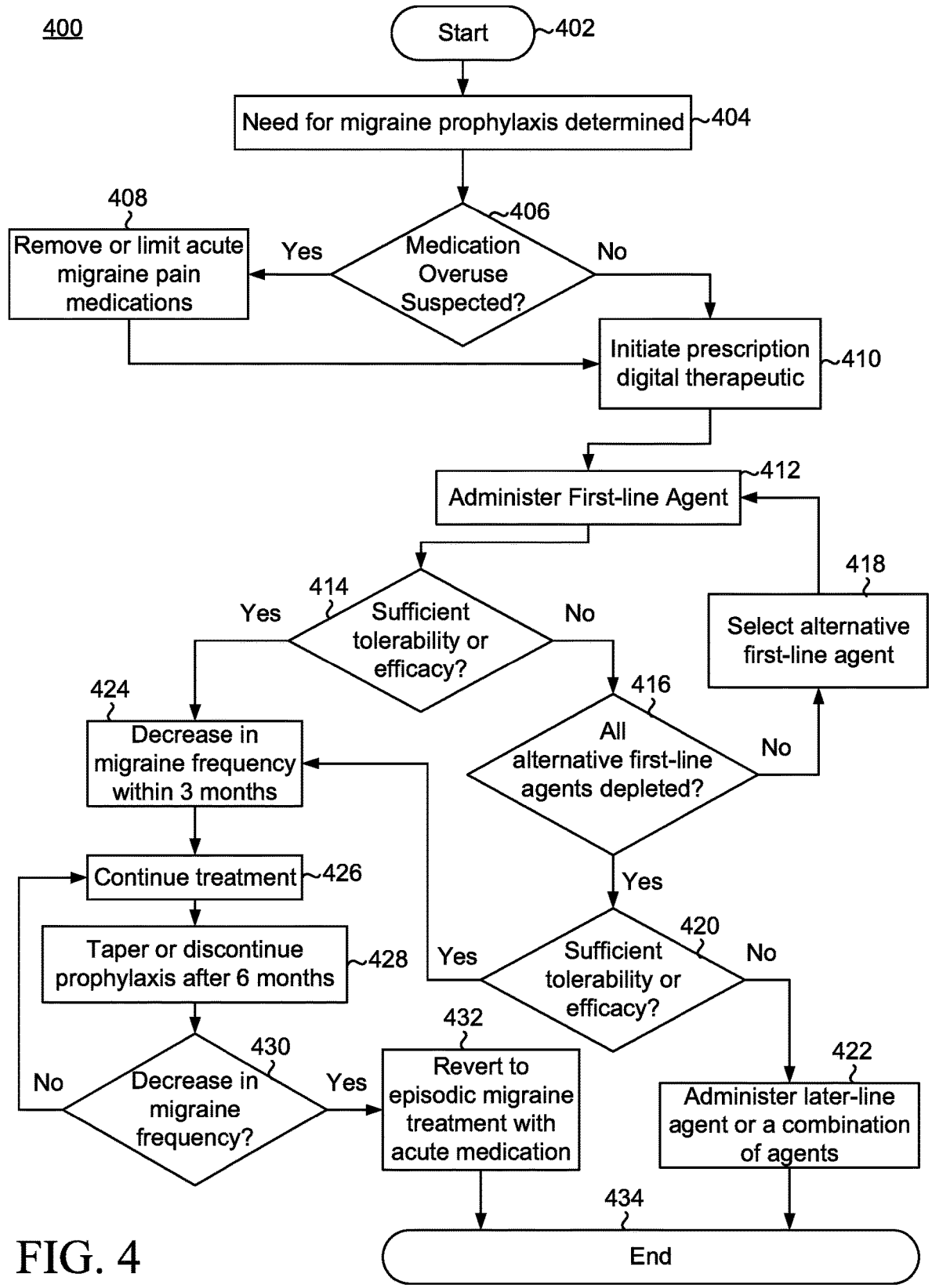
FIG. 4 is a flowchart illustrating a method for determining a medication-based treatment to address symptoms associated with migraines.

Referring to FIG. 4, a graphical flowchart illustrating a method 400 for determining a medication-based treatment is illustrated. The method 400 may be executed by the prescription digital therapeutic 120 (e.g., by execution of the patient application 103 and the migraine therapy application 160). The prescription digital therapeutic 120 is configured to start the method 400 at 402 and proceeds to step 404 where the prescription digital therapeutic 120 is configured to determine that the patient requires medication-based prophylaxis. This determination is based on a variety of factors, including the input data 224, any suitable input from the HCP 109, etc. At 406, the prescription digital therapeutic 120 is configured to determine whether medication overuse is suspected. Similarly, this determination may be based on a variety of factors, such as those set forth above. If the prescription digital therapeutic 120 determines that medication overuse is suspected, then at 408, the prescription digital therapeutic 120 is configured to remove or limit acute migraine pain medications before initiating (i.e., allowing the patient 101 to access) the prescription digital therapeutic, including the medication-based prophylaxis and the migraine therapy application at 410. If, at 406, the prescription digital therapeutic 120 determines that medication overuse is not suspected, then the prescription digital therapeutic 120 proceeds to initiating the prescription digital therapeutic at 410.

At 412, the prescription digital therapeutic 120 is configured to administer a first-line agent (e.g., via the administration module 214) or recommend a recommended dosage of a first-line agent (e.g., via the recommendation module 212). The first-line agent may be selected from any suitable medication, such as a triptan, a CGRP inhibitor, an NSAID, etc., and the determination of which first-line agent to select may be tailored to the patient 101 based on the plurality of data gathered about the patient 101 or the prescription digital therapeutic 120 may set a default first-line agent.

At 414, the prescription digital therapeutic 120 is configured to determine whether the administered first-line agent had insufficient tolerability or efficacy, which may be based on input by the patient 101 and/or input by the HCP 109. If the prescription digital therapeutic 120 determines that the administered first-line agent had insufficient tolerability or efficacy, then the prescription digital therapeutic 120 is configured, at 416, to determine whether all alternative first-line agents have been depleted. For example, there may be a finite number of first-line agents available for the patient 101 due to limitation by the HCP 109 or limitation by market availability. If, at 416, the prescription digital therapeutic 120 determines that all of the alternative first-line agents have not been depleted, then, at 418, the prescription digital therapeutic 120 is configured to select an alternative first-line agent than what was originally administered, and return to 412 where the alternative first-line agent is administered (or recommended) to the patient 101.

If, at 416, the prescription digital therapeutic 120 determines that all of the alternative first-line agents have been depleted, then, at 420, the prescription digital therapeutic 120 determines whether all of the alternative first-line agents have insufficient tolerability or efficacy. If, at 420, the prescription digital therapeutic 120 determines that all of the alternative first-line agents have insufficient tolerability or efficacy, then the prescription digital therapeutic 120, at 422, administers a later-line agent or a combination of agents, including first-line agents and/or later-line agents, and then the method 400 ends at 434. The later-line agent(s) may be any suitable medication, including a triptan, a CGRP inhibitor, an NSAID, etc.

If, at 414, the prescription digital therapeutic 120 determines that the administered first-line agent (whether the original first-line agent or a subsequent alternative first-line agent) has sufficient tolerability or efficacy, then the prescription digital therapeutic 120 is configured to proceed to 424 where it monitors the frequency of migraines experienced by the patient 101 over the next 3 months, which, because of the sufficient tolerability or efficacy of the first-line agent, the migraine frequency should decrease over the next 3 months. The prescription digital therapeutic 120 is configured to continue the treatment at 426 and taper or discontinue the prophylaxis after 6 months at 428.

At 430, the prescription digital therapeutic 120 is configured to determine whether, after tapering or discontinuing the prophylaxis after 6 months, the patient 101 has experienced a decrease in migraine frequency. If the prescription digital therapeutic 120 determines, at 430, that there has not been a decrease in migraine frequency, then the prescription digital therapeutic 120 is configured to return to 426 where the treatment is continued. If the prescription digital therapeutic 120 determines, at 430, that there has been a decrease in migraine frequency, then the prescription digital therapeutic 120 is configured to proceed to 432 where the patient 101 is prescribed episodic migraine treatment with acute medication as necessary and the method 400 ends at 434.

Figure 5:
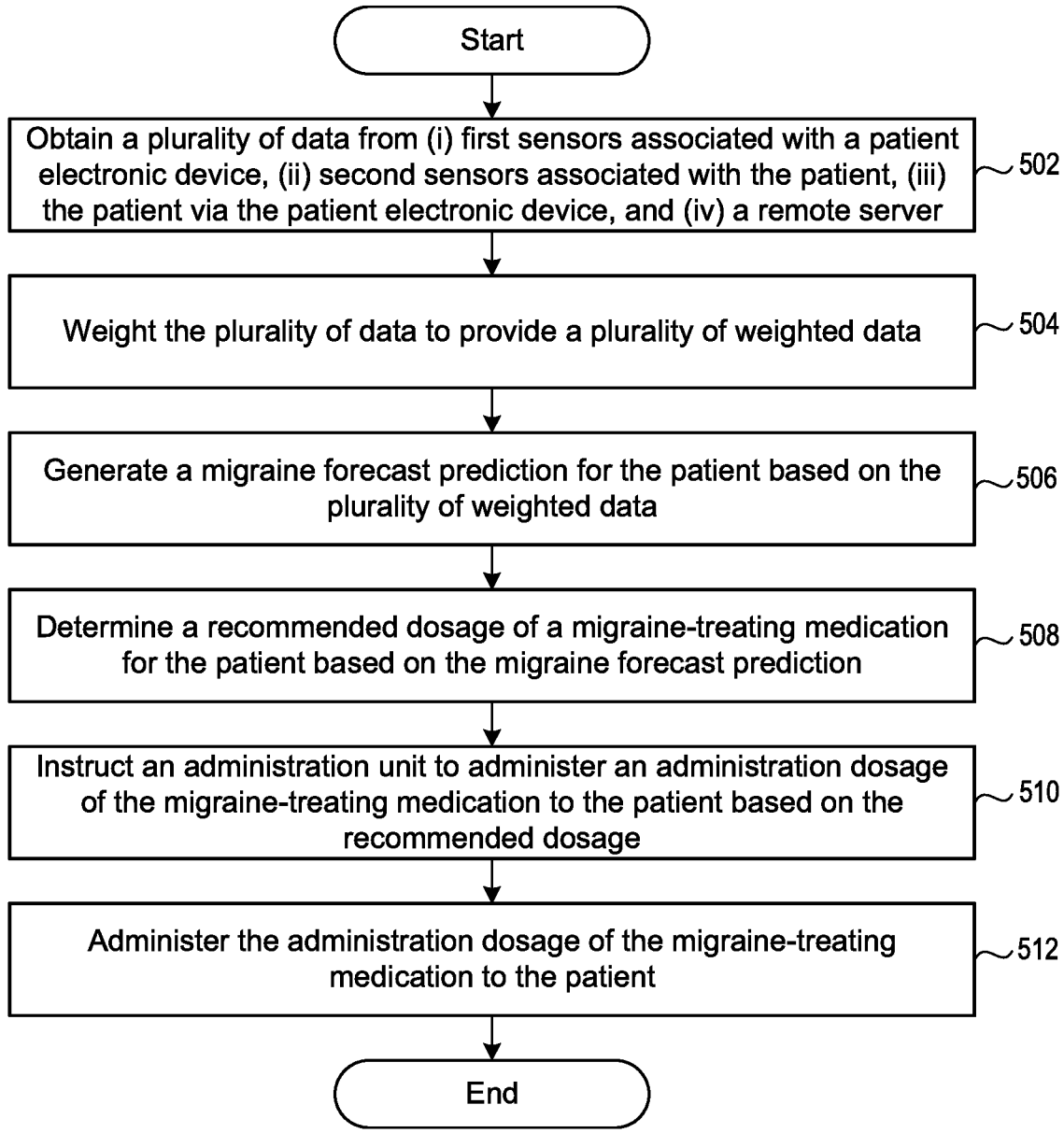
FIG. 5 is a flowchart illustrating a method for implementing a prescription digital therapeutic configured to treat symptoms associated with migraines, in accordance with an exemplary embodiment of the present disclosure.

Referring to FIG. 5, a flowchart illustrating a method 500 for implementing the prescription digital therapeutic 120 is generally shown. The method 500 includes, at 502, obtaining a plurality of data from (i) first sensors associated with a patient electronic device, (ii) second sensors associated with the patient, (iii) the patient via the patient electronic device, and (iv) a remote server. The method 500 includes, at 504, weighting the plurality of data to provide a plurality of weighted data. The method 500 includes, at 506, generating a migraine forecast prediction for the patient based on the plurality of weighted data. The method 500 includes, at 508, determining a recommended dosage of a migraine-treating medication for the patient based on the migraine forecast prediction. The method 500 includes, at 510, instructing an administration unit to administer an administration dosage of the migraine-treating medication to the patient based on the recommended dosage. The method 500 includes, at 512, administering the administration dosage of the migraine-treating medication to the patient. It should be understood that the method 500 may include additional or fewer steps than those shown and described, and certain steps may be omitted or performed in any suitable order.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Figure 6:
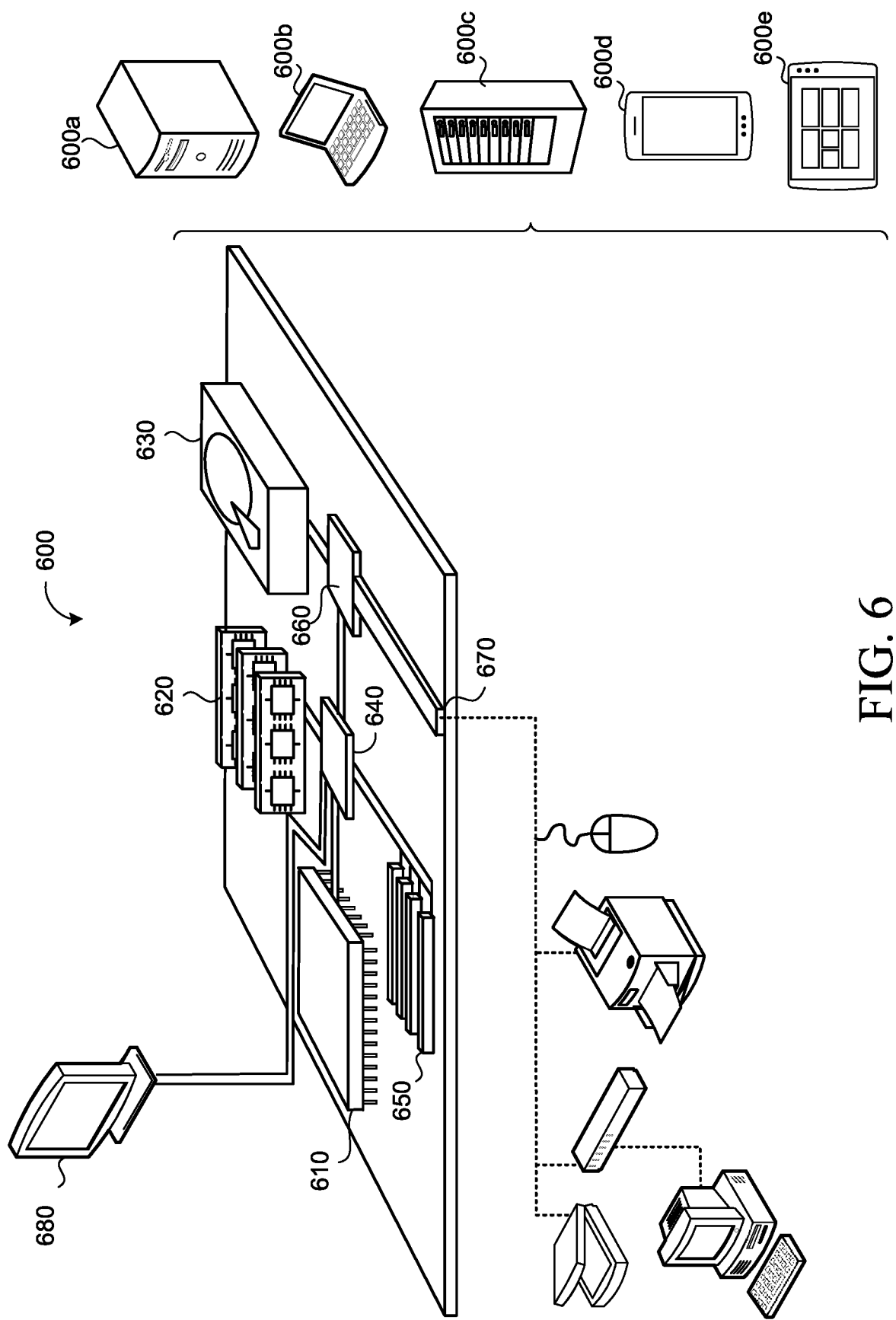
FIG. 6 is a schematic view of an example computing device that may be used to implement the systems and methods described herein.

FIG. 6 is schematic view of an example computing device 600 that may be used to implement the systems and methods described in this document. The computing device 600 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 600 includes a processor 610, memory 620, a storage device 630, a high-speed interface/controller 640 connecting to the memory 620 and high-speed expansion ports 650, and a low speed interface/controller 660 connecting to a low speed bus 670 and a storage device 630. Each of the components 610, 620, 630, 640, 650, and 660, are interconnected using various busses, and may be mounted on a common motherboard or in other manners as appropriate. The processor 610 can process instructions for execution within the computing device 600, including instructions stored in the memory 620 or on the storage device 630 to display graphical information for a graphical user interface (GUI) on an external input/output device, such as display 680 coupled to high speed interface 640. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 620 stores information non-transitorily within the computing device 600. The memory 620 may be a computer-readable medium, a volatile memory unit(s), or non-volatile memory unit(s). The non-transitory memory 620 may be physical devices used to store programs (e.g., sequences of instructions) or data (e.g., program state information) on a temporary or permanent basis for use by the computing device 600. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 630 is capable of providing mass storage for the computing device 600. In some implementations, the storage device 630 is a computer-readable medium. In various different implementations, the storage device 630 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 620, the storage device 630, or memory on processor 610.

The high speed controller 640 manages bandwidth-intensive operations for the computing device 600, while the low speed controller 660 manages lower bandwidth-intensive operations. Such allocation of duties is exemplary only. In some implementations, the high-speed controller 640 is coupled to the memory 620, the display 680 (e.g., through a graphics processor or accelerator), and to the high-speed expansion ports 650, which may accept various expansion cards (not shown). In some implementations, the low-speed controller 660 is coupled to the storage device 630 and a low-speed expansion port 690. The low-speed expansion port 690, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 600a or multiple times in a group of such servers 600a, as a laptop computer 600b, as part of a rack server system 600c, as a mobile device 600d (such as a smart phone), or as a tablet computer 600e.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A system comprising:
a patient electronic device comprising:
data processing hardware; and
non-transitory memory hardware in communication with the data processing hardware, the memory hardware storing instructions that when executed on the data processing hardware cause the data processing hardware to perform operations comprising:
executing a prescription digital therapeutic by administering cognitive behavioral therapy through a series of graphical user interfaces of the prescription digital therapeutic which update in real-time to provide presentations via the patient electronic device as an interactive display on a display of the patient electronic device as a cognitive thinking game interface, the cognitive thinking game interface between the patient and the prescription digital therapeutic being configured to treat symptoms associated with migraines experienced by a patient through interaction with a game environment executed by a CBT module, wherein executing the prescription digital therapeutic comprises:
obtaining a plurality of data from (i) first sensors associated with the patient electronic device, (ii) the patient via the patient electronic device receiving one or more inputs from the patient through interaction with the game environment, and (iii) a remote server;
weighting the plurality of data to provide a plurality of weighted data;
generating a migraine forecast prediction for the patient based on the plurality of weighted data;
determining a recommended dosage of a migraine-treating medication for the patient based on the migraine forecast prediction, the migraine-treating medication including one of a triptan or a calcitonin gene-related peptide (CGRP) inhibitor; and
instructing an administration unit to administer an administration dosage of the migraine-treating medication to the patient based on the recommended dosage.

2. The system of claim 1, further comprising the administration unit, wherein the administration unit is configured to administer the administration dosage of the migraine-treating medication to the patient based on the instructions.

3. The system of claim 2, wherein the administration unit performs operations comprising:
administering the administration dosage of the migraine-treating medication to the patient.

4. The system of claim 1, wherein executing the prescription digital therapeutic further comprises obtaining the plurality of data from second sensors associated with the patient, the second sensors comprising one or more of: (i) a heart rate monitor, (ii) a blood pressure monitor, (iii) a sleep monitor, (iv) an electrodermal activity monitor, (v) a skin temperature sensor, and (vi) a sweat monitor.

5. The system of claim 1, wherein the first sensors associated with the patient electronic device comprise one or more of: (i) an accelerometer, (ii) a proximity sensor, (iii) an activity monitor, and (iv) a location system.

6. The system of claim 1, wherein the plurality of data obtained from the patient via the input device comprise one or more of: (i) a migraine log, (ii) a migraine intensity indicator, (iii) a successful relief strategy, and (iv) a migraine-treating medication log.

7. The system of claim 1, wherein the plurality of data obtained from the remote server comprise one or more of: (i) a temperature, (ii) a humidity, (iii) a cloud cover, and (iv) a barometric pressure.

8. The system of claim 1, wherein weighting the plurality of data comprises assigning a first weight to a first data of the plurality of data and a second weight different than the first weight to a second data of the plurality of data.

9. The system of claim 1, wherein the administration unit comprises one or more of: (i) a delivery pump, (ii) an injection unit, (iii) an implant, (iv) an oral absorption unit, (v) an inhaler, and (vi) a nasal injector.

10. A method comprising:
executing a prescription digital therapeutic by administering cognitive behavioral therapy through a series of graphical user interfaces of the prescription digital therapeutic which update in real-time to provide presentations via a patient electronic device as an interactive display on a display of the patient electronic device as a cognitive thinking game interface, the cognitive thinking game interface between the patient and the prescription digital therapeutic being configured to treat symptoms associated with migraines experienced by a patient through interaction with a game environment executed by the CBT module, wherein executing the prescription digital therapeutic comprises:
obtaining, by data processing hardware, a plurality of data from (i) first sensors associated with the patient electronic device, (ii) the patient via the patient electronic device receiving one or more inputs from the patient through interaction with the game environment, and (iii) a remote server;
weighting, by the data processing hardware, the plurality of data to provide a plurality of weighted data;
generating, by the data processing hardware, a migraine forecast prediction for the patient based on the plurality of weighted data;
determining, by the data processing hardware, a recommended dosage of a migraine-treating medication for the patient based on the migraine forecast prediction, the migraine-treating medication including one of a triptan or a calcitonin gene-related peptide (CGRP) inhibitor; and
instructing, by the data processing hardware, an administration unit to administer an administration dosage of the migraine-treating medication to the patient based on the recommended dosage.

11. The method of claim 10, wherein the administration unit is configured to administer the administration dosage of the migraine-treating medication to the patient based on the instructions.

12. The method of claim 11, wherein executing the prescription digital therapeutic further comprises administering, by the administration unit, the administration dosage of the migraine-treating medication to the patient.

13. The method of claim 10, wherein executing the prescription digital therapeutic further comprises obtaining the plurality of data from second sensors associated with the patient, the second sensors comprising one or more of: (i) a heart rate monitor, (ii) a blood pressure monitor, (iii) a sleep monitor, (iv) an electrodermal activity monitor, (v) a skin temperature sensor, and (vi) a sweat monitor.

14. The method of claim 10, wherein the first sensors associated with the patient electronic device comprise one or more of: (i) an accelerometer, (ii) a proximity sensor, (iii) an activity monitor, and (iv) a location system.

15. The method of claim 10, wherein the plurality of data obtained from the patient via the input device comprise one or more of: (i) a migraine log, (ii) a migraine intensity indicator, (iii) a successful relief strategy, and (iv) a migraine-treating medication log.

16. The method of claim 10, wherein the plurality of data obtained from the remote server comprise one or more of: (i) a temperature, (ii) a humidity, (iii) a cloud cover, and (iv) a barometric pressure.

17. The method of claim 10, wherein weighting the plurality of data comprises assigning a first weight to a first data of the plurality of data and a second weight different than the first weight to a second data of the plurality of data.

18. The method of claim 10, wherein the administration unit comprises one or more of: (i) a delivery pump, (ii) an injection unit, (iii) an implant, (iv) an oral absorption unit, (v) an inhaler, and (vi) a nasal injector.

19. The system of claim 1, wherein the prescription digital therapeutic comprises a plurality of modules including at least one of: (i) an input module, (ii) a data weighting module, (iii) a prediction module, (iv) an education module, (v) a treatment and recommendation module, (vi) an administration module, (vii) or a cognitive behavioral therapy module.

20. The method of claim 10, wherein the prescription digital therapeutic comprises a plurality of modules including at least one of: (i) an input module, (ii) a data weighting module, (iii) a prediction module, (iv) an education module, (v) a treatment and recommendation module, (vi) an administration module, (vii) or a cognitive behavioral therapy module.

* * * * *